US012653902B2

(12) United States Patent
Huang et al.

(10) Patent No.: US 12,653,902 B2
(45) Date of Patent: *Jun. 16, 2026**

(54) PHOTO-IMMUNOCONJUGATE FORMULATIONS AND METHODS OF TREATMENT RELATING THERETO

(71) Applicant: University of Maryland, College Park, College Park, MD (US)

(72) Inventors: Huang-Chiao Huang, Washington, DC (US); Barry Jiahao Liang, Gaithersburg, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/344,712

(22) Filed: Jun. 29, 2023

(65) Prior Publication Data

US 2024/0108724 A1 Apr. 4, 2024

Related U.S. Application Data

(63) Continuation of application No. 16/878,873, filed on May 20, 2020, now Pat. No. 11,759,521.

(60) Provisional application No. 62/850,228, filed on May 20, 2019.

(51) Int. Cl.
| | |
|---|---|
| *A61K 47/68* | (2017.01) |
| *A61K 31/4745* | (2006.01) |
| *A61K 41/00* | (2020.01) |
| *A61K 47/69* | (2017.01) |
| *C07K 16/28* | (2006.01) |
| *C07K 16/32* | (2006.01) |

(52) U.S. Cl.
CPC ...... *A61K 47/6849* (2017.08); *A61K 41/0057* (2013.01); *A61K 47/6803* (2017.08); *A61K 47/6851* (2017.08); *A61K 47/6929* (2017.08); *A61K 31/4745* (2013.01); *C07K 16/2863* (2013.01); *C07K 16/32* (2013.01)

(58) Field of Classification Search
None
See application file for complete search history.

(56) References Cited

U.S. PATENT DOCUMENTS

| | | | | |
|---|---|---|---|---|
| 9,358,306 B2 * | 6/2016 | Kobayashi | ......... | A61K 47/6803 |
| 11,759,521 B2 * | 9/2023 | Huang | ............... | A61K 47/6803 |
| | | | | 424/1.53 |
| 2002/0197262 A1 | 12/2002 | Hasan et al. | | |
| 2018/0133343 A1 | 5/2018 | Irvine et al. | | |

FOREIGN PATENT DOCUMENTS

| | | | |
|---|---|---|---|
| WO | | 2016191556 A1 | 12/2016 |
| WO | WO 2016/191556 | | 12/2016 |
| WO | | 2023044436 A1 | 3/2023 |
| WO | | 2023173087 A1 | 9/2023 |

OTHER PUBLICATIONS

Liang et al., J Nanobiotechnol 18: 1-14 (Year: 2020).*
Abrahamse, H. et al. (2016) *"New Photosensitizers For Photodynamic Therapy,"* Biochem. J. 473:347-364.
Abu-Yousif, A.O. et al. (2012) *"Epidermal Growth Factor Receptor-Targeted Photosensitizer Selectively Inhibits EGFR Signaling And Induces Targeted Phototoxicity In Ovarian Cancer Cells,"* Cancer Letters 321:120-127.
Baglo, Y. et al. (2019) *"Porphyrin-Lipid Assemblies And Nanovesicles Overcome ABC Transporter-Mediated Photodynamic Therapy Resistance In Cancer Cells,"* Cancer Letters 457:110-118.
Barua, S. et al. (2013) *"Synergistic Targeting Of Cell Membrane, Cytoplasm, And Nucleus Of Cancer Cells Using Rod-Shaped Nanoparticles,"* ACS Nano 2013, 7:9558-9570.
Batist, G. et al. (2009) *"Safety, Pharmacokinetics, And Efficacy Of CPX-1 Liposome Injection In Patients With Advanced Solid Tumors,"* Clin. Cancer Res 15(2):692-700.
Burley, T.A. et al. (2018) *"Near-Infrared Photoimmunotherapy Targeting EGFR-Shedding New Light On Glioblastoma Treatment,"* Int. J. Cancer 142:2363-2374.
Carter KA et al. (2016) *"Sphingomyelin Liposomes Containing Porphyrin-Phospholipid For Irinotecan Chemophototherapy,"* Theranostics 6:2329-2336.
Chabner, B.A. et al. (2005) *"Timeline: Chemotherapy And The War On Cancer,"* Nat Rev. Cancer 5:65-72.
Chakravarti, A. et al. (2013) *"RTOG 0211: A Phase 1/2 Study Of Radiation Therapy With Concurrent Gefitinib For Newly Diagnosed Glioblastoma Patients,"* Int. J. Radiat. Oncol. Biol. Phys. 85:1206-1211.
Chen, B. et al. (2005) *"Liposomal Delivery Of Photosensitising Agents,"* Expert Opin. Drug Deliv. 2:477-487 (Abstract Only).
Chou, T.C. et al. (1984) *"Quantitative Analysis Of Dose-Effect Relationships: The Combined Effects Of Multiple Drugs Or Enzyme Inhibitors,"* Adv. Enzyme Regul. 22:27-55 (Abstract Only).
Chou, T.C. (2006) *"Theoretical Basis, Experimental Design, And Computerized Simulation Of Synergism And Antagonism In Drug Combination Studies,"* Pharmacol. Rev. 58:621-681 (Abstract Only).
Chowdhary, R.K. et al. (2003) *"Drug Release Characteristics Of Lipid Based Benzoporphyrin Derivative,"* J. Pharm. Pharmaceut. Sci. 6:13-19.
Drummond, D.C. et al. (2006) *"Development of a Highly Active Nanoliposomal Irinotecan Using a Novel Intraliposomal Stabilization Strategy,"* Cancer Res. 66(6):3271-3277.

(Continued)

*Primary Examiner* — Phuong Huynh
(74) *Attorney, Agent, or Firm* — HYLTON-RODIC LAW PLLC

(57) ABSTRACT

The present disclosure relates to photo-immunoconjugate formulations comprising a nanoparticle carrier comprising first and second therapeutic agents coupled to the nanoparticle carrier, and a photosensitizer molecule coupled to the first therapeutic agent or the nanoparticle carrier, and methods of treating cancer via administration of the photo-immunoconjugate formulations.

14 Claims, 15 Drawing Sheets
(1 of 15 Drawing Sheet(s) Filed in Color)

(56) References Cited

OTHER PUBLICATIONS

Edwards, B.M. et al. (2003) "*The Remarkable Flexibility of the Human Antibody Repertoire; Isolation of Over One Thousand Different Antibodies to a Single Protein, BLyS,*" J. Molec. Biol. 334(1):103-118.

Feldman, E.J. et al. (2011) "*First-In-Man Study Of CPX-351: A Liposomal Carrier Containing Cytarabine And Daunorubicin In A Fixed 5:1 Molar Ratio For The Treatment Of Relapsed And Refractory Acute Myeloid Leukemia,*" J. Clin. Oncol. 29(8):979-998.

Fernald, K. et al. (2013) "*Evading Apoptosis In Cancer,*" Trends Cell. Biol. 23(12):620-633.

Ferrari, M. (2005) "*Cancer Nanotechnology: Opportunities And Challenges,*" Nat. Rev. Cancer 5:161-171.

Gallagher-Colombo, S.M. et al. (2015) "*Erlotinib Pretreatment Improves Photodynamic Therapy Of Non-Small Cell Lung Carcinoma Xenografts Via Multiple Mechanisms,*" Cancer Res. 75:3118-3126.

Garbuzenko, O.B. et al. (2010) "*Inhibition Of Lung Tumor Growth By Complex Pulmonary Delivery Of Drugs With Oligonucleotides As Suppressors Of Cellular Resistance,*" Proc. Natl. Acad. Sci. (U.S.A.) 107:10737-10742.

Geethadevi, A. et al. (2017) "*ERBB Signaling In Ctcs Of Ovarian Cancer And Glioblastoma,*" Genes & Cancer 8:746-751.

Gonzalez-Rodriguez, D. et al. (2015) "*Dynamics Of Receptor-Mediated Nanoparticle Internalization Into Endothelial Cells,*" Plos One 10:E0122097; pp. 1-23.

Hasselbalch, B. et al. (2010) "*Cetuximab, Bevacizumab, And Irinotecan For Patients With Primary Glioblastoma And Progression After Radiation Therapy And Temozolomide: A Phase II Trial,*" Neuro. Oncol. 12(5):508-516.

Hawe, A. et al. (2011) "*Taylor Dispersion Analysis Compared To Dynamic Light Scattering For The Size Analysis Of Therapeutic Peptides And Proteins And Their Aggregates,*" Pharm. Res. 28(9):2302-2310.

Herrlinger, U. et al. (2016) "*Bevacizumab Plus Irinotecan Versus Temozolomide In Newly Diagnosed 06-Methylguanine-DNA Methyltransferase Nonmethylated Glioblastoma: The Randomized GLARIUS Trial,*" J. Clin. Oncol. 34:1611-1619.

Huang, H.C. et al. (2014) "*The "Nano" World In Photodynamic Therapy,*" Austin J. Nanomed. Nanotechnol. 2(3):1020:1-8.

Huang, H.C. et al. (2016) "*Photodynamic Therapy Synergizes With Irinotecan To Overcome Compensatory Mechanisms And Improve Treatment Outcomes In Pancreatic Cancer,*" Cancer Res. 76:1066-1077.

Huang, H.C. et al. (2018) "*Immobilization Of Photo-Immunoconjugates On Nanoparticles Leads To Enhanced Light-Activated Biological Effects,*" Small 2018:E1800236; pp. 1-23.

Huang, H.C. et al. (2018) "*Mechanism-Informed Repurposing Of Minocycline Overcomes Resistance To Topoisomerase Inhibition For Peritoneal Carcinomatosis,*" Mol. Cancer Ther. 17:508-520.

Huang, H.C. et al. (2018) "*Photodynamic Priming Mitigates Chemotherapeutic Selection Pressures And Improves Drug Delivery,*" Cancer Res. 78:558-571.

Inglut, C.T. et al. (2020) "*Predictors And Limitations Of The Penetration Depth Of Photodynamic Effects In The Rodent Brain,*" Photochem. Photobiol. 96(2):301-309.

Inglut, C.T. et al. (2019) "*Systematic Evaluation Of Light-Activatable Biohybrids For Anti-Glioma Photodynamic Therapy,*" J. Clin. Med. 8(9):1269:1-20.

Jia, J. et al. (2009) "*Mechanisms Of Drug Combinations: Interaction And Network Perspectives,*" Nat. Rev. Drug Discov. 8(2):111-128.

Kessel, D. et al. (1997) "*The Role Of Subcellular Localization In Initiation Of Apoptosis By Photodynamic Therapy,*" Photochem. Photobiol. 65:422-426.

Kessel, D. et al. (1998) "*Mitochondrial Photodamage And PDT-Induced Apoptosis,*" J. Photochem. Photobiol. B 42:89-95.

Kessel, D. et al. (2001) "*Evidence That Bcl-2 Is The Target Of Three Photosensitizers That Induce A Rapid Apoptotic Response,*" Photochem. Photobiol. 74:318-322.

Kuo, L.J. et al. (2008) "*Gamma-H2AX—A Novel Biomarker For DNA Double-Strand Breaks,*" In Vivo 22:305-309.

Lloyd, C. et al. (2009) "*Modelling The Human Immune Response: Performance Of A $10^{11}$ Human Antibody Repertoire Against A Broad Panel Of Therapeutically Relevant Antigens,*" Protein Engineer. Des. Sel. 22:159-168.

Lopez, J.S et al. (2017) "*Combine And Conquer: Challenges For Targeted Therapy Combinations In Early Phase Trials,*" Nat. Rev. Clin. Oncol. 14:57-66.

Lovell, J.F. et al. (2011) "*Porphysome Nanovesicles Generated By Porphyrin Bilayers For Use As Multimodal Biophotonic Contrast Agents,*" Nature Materials 10:324-332.

Lucky, S.S. et al. (2015) "*Nanoparticles In Photodynamic Therapy,*" Chem. Rev. 115:1990-2042.

Luo, D. et al. (2017) "*Intrabilayer 64Cu Labeling Of Photoactivatable, Doxorubicin-Loaded Stealth Liposomes,*" ACS Nano 2017 11:12482-12491.

Malam, Y. et al. (2009) "*Liposomes And Nanoparticles: Nanosized Vehicles for Drug Delivery in Cancer,*" Trends Pharmacol. Sci. 30:592-599.

Mew, D. et al. (1983) "*Photoimmunotherapy: Treatment Of Animal Tumors With Tumor-Specific Monoclonal Antibody-Hematoporphyrin Conjugates,*" J. Immunol. 130:1473-1477 (Abstract Only).

Miller, C.R. et al. (1998) "*Liposome-Cell Interactions In Vitro: Effect Of Liposome Surface Charge On The Binding And Endocytosis Of Conventional And Sterically Stabilized Liposomes,*" Biochemistry 37:12875-12883.

Mitsunaga, M. et al. (2011) "*Cancer Cell-Selective In Vivo Near Infrared Photoimmunotherapy Targeting Specific Membrane Molecules,*" Nat. Med. 17:1685-1691.

Mudshinge, S.R. et al. (2011) "*Nanoparticles: Emerging Carriers For Drug Delivery,*" Saudi Pharm J. 19(3):129-141.

Neyns, B. et al. (2009) "*Stratified Phase II Trial Of Cetuximab In Patients With Recurrent High-Grade Glioma,*" Ann. Oncol. 20(9):1596-1603.

Normanno, N. et al. (2006) "*Epidermal Growth Factor Receptor (EGFR) Signaling In Cancer,*" Gene 366:2-16.

Obaid, G. et al. (2019) "*Nanolipid Formulations Of Benzoporphyrin Derivative: Exploring The Dependence Of Nanoconstruct Photophysics And Photochemistry On Their Therapeutic Index In Ovarian Cancer Cells,*" Photochem. Photobiol. 95:364-377.

Parchment, R.E. et al. (1998) "*Topoisomerase I Inhibitors And Drug Resistance,*" Cytotechnology 27:149-164.

Peer, D. et al. (2007) "*Nanocarriers As An Emerging Platform For Cancer Therapy,*" Nature Nanotechnology 2:751-760.

Peereboom, D.M. et al. (2010) "*Phase II Trial Of Erlotinib With Temozolomide And Radiation In Patients With Newly Diagnosed Glioblastoma Multiforme,*" J. Neuro. Oncol. 98:93-99.

Pigula, M. et al. (2019) "*Size-Dependent Tumor Response To Photodynamic Therapy And Irinotecan Monotherapies Revealed By Longitudinal Ultrasound Monitoring In An Orthotopic Pancreatic Cancer Model,*" Photochem. Photobiol. 95(1):378-386.

Pommier, Y. (2006) "*Topoisomerase I Inhibitors: Camptothecins And Beyond,*" Nat. Rev. Cancer 6:789-802.

Posadas, E.M. et al. (2007) "*A Phase II And Pharmacodynamic Study Of Gefitinib In Patients With Refractory Or Recurrent Epithelial Ovarian Cancer,*" Cancer 109:1323-1330.

Pudlarz, A. et al. (2018) "*Nanoparticles as Carriers of Proteins, Peptides and Other Therapeutic Molecules,*" Open Life Sci. 13:285-298.

Puertas, S. et al. (2010) "*Designing Novel Nano-Immunoassays: Antibody Orientation Versus Sensitivity,*" J. Phys. D: Applied Physics 43(47):4012:1-13.

Rizvi, I. et al. (2010) "*Synergistic Enhancement Of Carboplatin Efficacy With Photodynamic Therapy In A Three-Dimensional Model For Micrometastatic Ovarian Cancer,*" Cancer Res. 70(22):9319-9328.

Saif, M.W. (2014) "*MM-398 Achieves Primary Endpoint Of Overall Survival In Phase III Study In Patients With Gemcitabine Refractory Metastatic Pancreatic Cancer,*" Jop 2014, 15:278-279.

(56) References Cited

OTHER PUBLICATIONS

Sakhrani, N.M. et al. (2013) *"Organelle Targeting: Third Level Of Drug Targeting,"* Drug Design, Develop. Ther. 7:585-599.

Sato, K.et al. (2015) *"Near Infrared Photoimmunotherapy In The Treatment Of Disseminated Peritoneal Ovarian Cancer,"* Mol. Cancer Ther. 14:141-150.

Savellano, M.D. et al. (2003) *"Targeting Cells That Overexpress The Epidermal Growth Factor Receptor With Polyethylene Glycolated BPD Verteporfin Photosensitizer Immunoconjugates,"* Photochem. Photobiol. 77:431-439.

Savellano, M.D. et al. (2005) *"Photochemical Targeting Of Epidermal Growth Factor Receptor: A Mechanistic Study,"* Clin. Cancer Res. 11:1658-1668.

Schmidt, S. et al. (1992) *"Clinical Use Of Photodynamic Therapy In Gynecologic Tumor Patients—Antibody-Targeted Photodynamic Laser Therapy As A New Oncologic Treatment Procedure,"* Zentralbl. Gynakol. 114:307-331 (Abstract Only).

Schneider, C.A. et al. (2012) *NIH Image To Imagej: 25 Years Of Image Analysis.* Nat. Methods 9:671-675.

Secord, A.A. et al. (2008) *"Phase II Trial Of Cetuximab And Carboplatin In Relapsed Platinum-Sensitive Ovarian Cancer And Evaluation Of Epidermal Growth Factor Receptor Expression: A Gynecologic Oncology Group Study,"* Gynecol. Oncl. 108:493-499.

Seshacharyulu, P. et al. (2012) *"Targeting The EGFR Signaling Pathway In Cancer Therapy,"* Expert Opin. Ther. Targets 16:15-31.

Shi, J. et al. (2017) *"Cancer Nanomedicine: Progress, Challenges And Opportunities,"* Nature Rev. Cancer 17:20-37.

Shim, G. et al. (2011) *"Trilysinoyl Oleylamide-Based Cationic Liposomes For Systemic Co-Delivery Of siRNA And An Anticancer Drug,"* J. Control Release 155:60-66.

Sigismund S et al., *Emerging Functions Of The EGFR In Cancer.* Molecular Oncol 2018, 12:3-20.

Spring, B.Q. et al. (2014) *"Selective Treatment And Monitoring Of Disseminated Cancer Micrometastases In Vivo Using Dual-Function, Activatable Immunoconjugates,"* Proc. Natl. Acad. Sci. (U.S.A.) 111(10): E933-E942.

Spring, B.Q. et al. (2015) *"The Role Of Photodynamic Therapy In Overcoming Cancer Drug Resistance,"* Photochem. Photobiol. Sci. 14:1476-149.

Tardi, P.G. et al. (2009) *"Drug Ratio-Dependent Antitumor Activity Of Irinotecan And Cisplatin Combinations In Vitro And In Vivo,"* Mol. Cancer Ther. 8:2266-2275.

Tolcher, A. W. et al. (2018) *"Improving Combination Cancer Therapy: The Combiplex((R)) Development Platform,"* Future Oncol. 14:1317-1332.

Vácha, R. et al. (2011) *"Receptor-Mediated Endocytosis Of Nanoparticles Of Various Shapes,"* Nano Lett 11:5391-5395.

Van Dam, G.M. et al. (2011) *"Intraoperative Tumor-Specific Fluorescence Imaging In Ovarian Cancer By Folate Receptor-Alpha Targeting: First In-Human Results,"* Nat. Med. 17:1315-1319.

Van Dongen, G.A. et al. (2004) *"Photosensitizer-Antibody Conjugates For Detection And Therapy Of Cancer,"* Adv. Drug Deliv. Rev. 56:31-52.

Vergote, I.B. et al. (2014) *"Randomized Phase III Study Of Erlotinib Versus Observation In Patients With No Evidence Of Disease Progression After First-Line Platin-Based Chemotherapy For Ovarian Carcinoma: A European Organisation For Research And Treatment Of Cancer-Gynaecological Cancer Group, And Gynecologic Cancer Intergroup Study,"* J. Clin. Oncol. 32:320-326.

Vredenburgh, J.J. et al. (2009) *"Experience With Irinotecan For The Treatment Of Malignant Glioma,"* Neuro-Oncology 11:80-91.

Weinandy, A. et al. (2014) *"Cetuximab Induces Emel-Mediated DNA Repair: A Novel Mechanism For Cetuximab Resistance,"* Neoplasia (New York, NY) 16:207-220.

Wonder, E. et al. (2018) *"Competition Of Charge-Mediated And Specific Binding By Peptide-Tagged Cationic Liposome-DNA Nanoparticles In Vitro And In Vivo,"* Biomaterials 166:52-63.

Wu, J. et al. (2007) *Reversal Of Multidrug Resistance By Transferrin-Conjugated Liposomes Co-Encapsulating Doxorubicin And Verapamil,* J. Pharm. Pharmaceut. Sci. 10(3):350-357.

Yang, Y. et al. (2012) *"Nanoparticle Delivery Of Pooled siRNA For Effective Treatment Of Non-Small Cell Lung Cancer,"* Mol. Pharm. 9(8):2280-2289.

Yao, Y. et al. (2020) *"Nanoparticle-Based Drug Delivery in Cancer Therapy and Its Role in Overcoming Drug Resistance,"* Front. Mol. Biosci. 7:193:1-14.

Peer et al., "Nanocarriers as an Emerging Platform for Cancer Therapy," Nature Nanotechnology 2: 751-760, (Year: 2007).

Peereboom et al., "Phase II Trial of Erlotinib with Temozolomide and Radiation in Patients with Newly Diagnosed Glioblastoma Multiforme," J. Neuro. Oncol. 98: 93-99, (Year: 2010).

Pigula et al., "Size-Dependent Tumor Response to Photodynamic Therapy and Irinotecan Monotherapies Revealed by Longitudinal Ultrasound Monitoring in an Orthotopic Pancreatic Cancer Model," Photochem. Photobiol. 95(1): 378-386, (Year: 2019).

Pommier, "Topoisomerase I Inhibitors: Camptothecins and Beyond," Nat. Rev. Cancer 6: 789-802, (Year: 2006).

Posadas et al., "A Phase II and Pharmacodynamic Study of Getfitnib in Patients with Refractory or Recurrent Epithelial Ovarian Cancer," Cancer 109: 1323-1330, (Year: 2007).

Pudlarz et al., "Nanoparticles as Carriers of Proteins, Peptides and Other Therapeutic Molecules," Open Life Sci. 13: 285-298, (Year: 2018).

Puertas et al., "Designing Novel Nano-Immunoassays: Antibody Orientation Versus Sensitivity," J. Phys. D: Applied Physics 43(47): 4012: 1-13, (Year: 2010).

Rizvi et al., "Synergystic Enhancement of Carboplatin Efficacy with Photodynamic Therapy in a Three-Dimensional Model for Micometastatic Ovarian Cancer," Cancer Res. 70(22): 9319-9328, (Year: 2010).

Saif, "MM-398 Achieves Primary Endpoint of Overall Survival in Phase III Study in Patients with Gemcitabine Refractory Metastatic Pancreatice Cancer," Jop 2014, 15: 278-279, (Year: 2014).

Sakhrani et al., "Organelle Targeting: Third Level of Drug Targeting," Drug Design, Develop Ther. 7: 585-599, (Year: 2013).

Sato et al., "Near Infrared Photoimmunotherapy in the Treatment of Disseminated Peritoneal Ovarian Cancer," Mol. Cancer Ther. 14: 141-150, (Year: 2015).

Savellano et al., "Photochemical Targeting of Epidermal Growth Factor Receptor: a Mechanistic Study," Clin. Cancer Res. 11: 1658-1668, (Year: 2005).

Savellano et al., "Targeting Cells that Overexpress the Epidermal Growth Factor Receptor with Polyethylene Glycolated BPD Verteporfin Photosensitizer Immunoconjugates," Photochem. Photobiol. 77: 431-439, (Year: 2003).

Schmidt et al., "Clinical Use of Photodynamic Therapy in Gynecologic Tumor Patients—Antibody-Targeted Photodynamic Laser Therapy as a New Oncologic Treatment Procedure," Zentralbl. Gynakol. 114: 307-331, (Year: 1992).

Schneider et al., "NIH Image to Imagej: 25 Years of Image Analysis," Nat. Methods 9: 671-675, (Year: 2012).

Alvarez Secord et al., "Phase II Trial of Cetuximab and Carboplatin in Relapsed Platinum-Sensitive Ovarian Cancer and Evaluation of Epidermal Growth Factor Receptor expression: a Gynecologic Oncology Group Study," Gynecol. Oncl. 108: 493-499, (Year: 2008).

Seshacharyulu et al., "Targeting the EGFR Signaling Pathway in Cancer Therapy," Expert Opin. Ther. Targets 16: 15-31, (Year: 2012).

Shi et al., "Cancer Nanomedicine: Progress, Challenges and Opportunities," Nature Rev. Cancer 17: 20-37, (Year: 2017).

Shim et al., "Trilysinoyl Oleylamide-Based Cationic Liposomes for Systemic CO-Delviery of siRNA and and Anticancer Drug," J. Control Release 155: 60-66, (Year: 2011).

Sigismund et al., "Emerging Functions of the EGFR in Cancer," Molecular Oncol 2018(12): 3-20, (Year: 2018).

Spring et al., "Selective Treatment and Monitoring of Disseminated Cancer Micrometastases in Vivo Using Dual-Funciton, Activatable Immunoconjugates," Proc. Natl. Acad. Sci. (U.S.A.) 111(10): E933-E942, (Year: 2014).

Spring et al., "The Role of Photodynamic Therapy in Overcoming Cancer Drug Resistance," Photochem. Photobiol. Sci. 14: 1476-1491, (Year: 2015).

(56)    References Cited

OTHER PUBLICATIONS

Tardi et al., "Drug Ratio-Dependent Antitumor Activity of Irinotecan and Cisplatin Combinations in Vitro and in Vivo," Mol. Cancer Ther. 8: 2266-2275, (Year: 2009).

Tolcher et al., "Improving Combination Cancer Therapy: the Combiplex® Development Platform," Future Oncol. 14: 1317-1332, (Year: 2018).

Vácha et al., "Receptor-Mediated Endocytosis of Nanoparticles of Various Shapes," Nano Lett 11: 5391-5395, (Year: 2011).

Van Dam et al., "Intraoperative Tumor-Specific Fluorescence Imaging in Ovarian Cancer by Golate Receptor-Alpha Targeting: First In-Human Results," Nat. Med. 17: 1315-1319, (Year: 2011).

Van Dongen et al., "Photosensitizer-Antibody Conjugates for Detection and Therapy of Cancer," Adv. Drug Deliv. Rev. 56: 31-52, (Year: 2004).

Vergote et al., "Randomized Phase III Study of Elrotinib Versus Observation in Patients with No Evidence of Disease Progression After First-Line Platin-Based Chemotherapy for Ovarian Carcinoma: a European Organisation for Research and Treatment of Cancer—Gynaecological Cancer Group, and Gynecologic Cancer Intragroup Study," J. Clin. Oncol. 32: 320-326, (Year: 2014).

Vredenburgh et al., "Experience with Irinotecan for the Treatment of Malignant Glioma," Neuro-Oncology 11: 80-91, (Year: 2009).

Weinandy et al., "Cetuximab Induces Emel-Mediated DNA Repair: A Novel Mechanism for Cetuximab Resistance," Neoplasia (New York, NY) 16: 207-220, (Year: 2014).

Wonder et al., "Competition of Charge-Mediated and Specific Binding by Peptide-Tagged Catatonic Liposome-DNA Nanoparticles in Vitro and in Vivo," Biomaterials 166: 52-63, (Year: 2018).

Wu et al., "Reversal of Multidrug Resistance by Transferrin-Conjugated Liposomes Co-Encapsulating Doxorubicin and Verapamil<" J. Pharm. Pharmaceut. Sci. 10(3): 350-357, (Year: 2007).

Yang et al., "Nanoparticle Delivery of Pooled siRNA for Effective Treatment of Non-Small Cell Lung Cancer," Mol. Pharm. 9(8): 2280-2289, (Year: 2012).

Yao et al., "Nanoparticle-Based Drug Delivery in Cancer Therapy and Its Role in Overcoming Drug Resistance," Front. Mol. Biosci. 7(193): 1-14, (Year: 2020).

Inglut et al., "Predictors and Limitations of the Penetration Depth of Photodynamic Effects in the Rodent Brain," Photochem Photobiol. 96(2): 301-309, (Year: 2020).

Abrahamse et al., "New Photozensitizers for Photodynamic Therapy," Biochem J. 473, 347-364, (Year: 2016).

Abu-Yousif et al., "Epidermal Growth Factor Receptor-Targeted Photosensitizer Selectively Inhibits EGFR Signaling and Induces Targeted Phototoxicity in Ovarian Cancer Cells," Cancer Letters, 321, 120-127, (Year: 2012).

Baglo et al., "Porphyrin-Lipid Assemblies and Nanovesicles Overcome ABC Transporter-Mediated Photodynamic Therapy Resistance in Cancer Cells," Cancer Letters, 457, 110-118.

Barua et al., "Synergistic Targeting of Cell Membrane, Cytoplasm, and Nucleus of Cancer Cells Using Rod-Shaped Nanoparticles," ACS Nano 2013(7): 692-700, (Year: 2013).

Batist et al., "Safety, Pharmacokinetics, and Efficacy of CPX-1 Liposome Injection in Patients with Advanced Tumors," Clin. Cancer Res, 15(2): 692-700, (Year: 2009).

Burley et al., "Near-Infrared Photoimmunotherapy Targeting EGFR-Shedding New Light on Glioblastoma Treatment," Int. J. Cancer 142: 2363-2374, (Year: 2018).

Carter et al., "Sphingomyelin Liposomes Containing Porphyrin-Phospholipid for Irinotecan Chemophototherapy," Theranostics 6: 2329-2336, (Year: 2016).

Chabner et al., "Timeline: Chemotherapy and the War on Cancer," Nat Rev. Cancer 5: 65-72, (Year: 2005).

Chakravarti et al., "RTOG 0211: A Phase 1/2 Study of Radiation Therapy with Concurrent Gefitinib for Newly Diagnosed Glioblastoma Patients," Int. J. Radiat. Oncol. Biol. Phys., 85: 1206-1211, (Year: 2013).

Chen et al., "Liposomal Delivery of Photosensitising Agents," Expert Opin. Drug Deliv. 2: 477-487 (Abstract Only), (Year: 2005).

Chou et al., "Quantitative Analysis of Dose-Effect Relationships: the Combined Effects of Multiple Drugs or Enzyme Inhibitors," Adv. Enzyme Regul, 22: 27-55, (Year: 1984).

Chou et al., "Theoretical Basis, Experimental Design, and Computerized Stimulation of Synergism and Anatogonism in Drug Combination Studies," Pharmacol. Rev. 58: 621-681, (Year: 2006).

Chowdhary et al., "Drug Release Characteristics of Lipid Based Benzoporphyrin Derivative," J. Pharm. Pharmaceuti. Sci. 6: 13-19, (Year: 2003).

Drummond et al., Cancer Res 66(6): 3271-3277 (Year: 2003).

Edwards et al., J. Mol Biol. 334(1)L 103-118 (Year: 2003).

Feldman et al., "First-In-Man Study of CPX-351: A Liposomal Carrier Containing Cytarabine and Daunorubicin in a Fixed 5:1 Molar Ratio for the Treatment of Relapsed and Refractory Acute Myeloid Leukemia," J. Clin. Oncol., 29(8): 979-998, (Year: 2011).

Fernald et al., "Evading Apoptosis in Cancer," Trends Cell. Biol. 23(12): 620-633, (Year: 2013).

Ferrari et al., "Cancer Nanotechnology: Opportunities and Challenges," Nat. Rev. Cancer 5: 161-171, (Year: 2005).

Gallagher-Colombo et al., "Erlotinib Pretreatment Improves Photodynamic Therapy of Non-Small Cell Lung Carcinoma Xenografts via Multiple Mechanisms," Cancer Res., 75: 3118-3126, (Year: 2015).

Garbuzenko et al., "Inhibition of Lung Tumor Growth by Complex Pulmonary Delivery of Drugs with Oligonucleotides as Suppresors of Cellular Resistance," Proc. Natl. Acad. Sci. (U.S.A.), 107: 10737-10742, (Year: 2010).

Geethadevi et al., "ERBB Signaling in Ctcs of Ovarian Cancer and Glioblastoma," Genes & Cancer, 8: 746-751, (Year: 2017).

Gonzalez-Rodriguez et al., "Dynamics of Receptor-Mediated Nanoparticle Internalization into Endothelial Cells," Plos One 10(E0122097): 1-23, (Year: 2015).

Hasselbalch et al., "Cetuximab, Bevacizumab, and Irinotecan for Patients with Primary Glioblastoma and Progression After Radiation Therapy and Temozolomide: A Phase II Trial," Neuro. Oncol., 12(5): 508-516, (Year: 2010).

Hawe et al., "Taylor Dispersion Analysis Compared to Dynamic Light Scattering for the Size Analysis of Therapeutic Peptides and Proteins and Their Aggregates," Pharm. Res., 28(9): 2302-2310, (Year: 2011).

Herrlinger et al., "Bevacizumab Plus Irinotecan Versus Temozolomide in Newly Diagnosed 06-Methylguanine-DNA Methyltransferase Nonmethylated Glioblastoma: the Randomized GLARIUS Trial," J. Clin. Oncol. 34: 1611-1619, (Year: 2016).

Huang et al., "Immobilization of Photo-Immunoconjugates on Nanoparticles Leads to Enhanced Light-Activated Biological Effects," Small 2018:E1800236, 1-23, (Year: 2018).

Huang et al., "Mechanism-Informed Repurposing of Minocycline Overcomes Resistance to Topoisomerase Inhibition for Peritoneal Carcinomatosis," Mol. Cancer Ther., 17: 508-520, (Year 2018).

Huang et al., "Photodynamic Priming Mitigates Chemotherapeutic Selection Pressures and Improves Drug Delivery," Cancer Res. 78: 558-571, (Year: 2018).

Huang et al., "Photodynamic Therapy Synergizes with Irinotecan to Overcome Compensatory Mechanisms and Improve Treatment Outcomes in Pancreatic Cancer," Cancer Res. 76: 1066-1077, (Year: 2016).

Huang et al., "The 'Nano' World in Photodynamic Therapy," Austin J. Nanomed. Nanotechnol., 2(3): 1020: 1-8, (Year: 2014).

Inglut et al., "Systematic Evaluation of Light-Activatable Biohybrids for Anti-Glioma Photodynamic Therapy," Photochem. Photobiol., 96(2): 301-309, (Year: 2020).

Jia et al., "Mechanisms of Drug Combinations: Interactions and Network Perspectives," Nat. Rev. Drug Discov. 8(2): 111-128, (Year: 2009).

Kessel et al., "Evidence That Bcl-2 is the Target of Three Photosensitizers That Induce a Rapid Apoptotic Response," Photochem. Photobiol. 74: 318-322, (Year: 2001).

Kessel et al., "Mitochondrial Photodamage and PDT-Induced Apoptosis," J. Photochem. Photobiol. B 42: 89-95, (Year: 1998).

Kessel et al., "The Role of Subcellular Localization in Initiation of Apoptosis by Photodynamic Therapy," Photochem. Photobiol. 65: 422-426, (Year: 1997).

(56) References Cited

OTHER PUBLICATIONS

Kuo et al., "Gamma-H2AX—A Novel Biomarker for DNA Double-Strand Breaks," In Vivo 22: 305-309 (Year: 2008).

Lloyd et al., "Modelling the Human Immune Response: Performance of a 10/\11 Human Antibody Repertoire Against a Broad Panel of Therapeutically Relevant Antigens," Protein Engineer, Des. Sel. 22: 159-168, (Year: 2009).

Lopez et al., "Combine and Conquer: Challenges for Targeted Therapy Combinations in Early Phase Trials," Nat. Rev. Clin. Oncol. 14: 57-66, (Year: 2017).

Lovell et al., "Porphysome Nanovesicles Generated by Porphyrin Bilayers for Use as Multimodal Biophotonic Contrast Agents," Nature Materials, 10: 324-332, (Year: 2011).

Lucky et al., "Nanoparticles in Photodynamic Therapy," Chem. Rev. 115: 1990-2042, (Year: 2015).

Luo et al., "Intrabilayer 64Cu Labeling of Photoactivatable, Doxorubicin-Loaded Stealth Liposomes," ACS Nano, 2017 (11): 12482-12491, (Year: 2017).

Malam et al., "Liposomes and Nanoparticles: Nanosized Vehicles for Drug Delivery in Cancer," Trends Pharmacol. Sci., 30: 592-599, (Year: 2009).

Mew et al., "Photoimmunotherapy: Treatment of Animal Tumors with Tumor-Specific Monoclonal Antibody-Hematoporphyrin Conjugates," J. Immunol. 130: 1473-1477, (Year: 1983).

Miller et al., "Liposome-Cell Interactions in Vitro: Effect of Liposome Surface Charge on the Binding and Endocytosis of Conventional and Sterically Stabilized Liposomes," Biochemistry, 37: 12875-12883, (Year: 1998).

Mitsunaga et al., "Cancer Cell-Selective in Vivo Near Infrared Photoimmunotherapy Targeting Specific Membrance Molecules," Nat. Med. 17: 1685-1691, (Year: 2011).

Mudshinge et al., "Nanoparticles: Emerging Carriers for Drug Delivery," Saudi Pharm J., 19(3): 129-141, (Year: 2011).

Neyns et al., "Stratified Phase II Trial of Cetuximab in Patients with Recurrent High-Grade Glioma," Ann. Oncol. 20 (9): 1596-1604, (Year: 2011).

Normanno et al., "Epidural Growth Factor Receptor (EGFR) Signaling in Cancer," Gene 366: 2-16, (Year: 2006).

Obaid et al., "Nanolipid Formulations of Benzoporphyrin Derivative: Exploring the Dependence of Nanoconstruct Photophysics and Photochemistry on Their Therapeutic Index in Ovarian Cancer Cells," Photochem. Photobiol. 95: 364-377, (Year: 2019).

Parchment et al., "Topoisomerase I Inhibitors and Drug Resistance," Cytotechnology 27: 149-164, (Year: 1998).

* cited by examiner a

Figure 13

PHOTO-IMMUNOCONJUGATE FORMULATIONS AND METHODS OF TREATMENT RELATING THERETO

CROSS-REFERENCE TO RELATED APPLICATION

This Application is a continuation of, and claims priority to, U.S. patent application Ser. No. 16/878,873 (filed on May 20, 2020), now U.S. Pat. No. 11,759,521, which application claims priority to U.S. Provisional Patent Application Ser. No. 62/850,228 (filed on May 20, 2019), which applications are each incorporated herein by reference in its entirety.

STATEMENT REGARDING FEDERALLY SPONSORED RESEARCH OR DEVELOPMENT

This invention was made with government support under R00 CA194269 awarded by the National Institutes of Health, The government has certain rights in the invention.

FIELD OF THE INVENTION

The present disclosure relates to photo-immunoconjugate formulations comprising a nanoparticle carrier comprising first and second therapeutic agents coupled to the nanoparticle carrier, and a photosensitizer molecule coupled to the first therapeutic agent or the nanoparticle carrier, and methods of treating cancer via administration of the photo-immunoconjugate formulations.

BACKGROUND OF THE INVENTION

Dysfunction of epidermal growth factor receptor (EGFR) has been associated with cancer development as well as disease progression due to its role in modulation of cell growth and survival (Seshacharyulu P et al., *Targeting the EGFR signaling pathway in cancer therapy*. Expert Opin Ther Targets 2012, 16:15-31). EGFR is overexpressed in numerous malignancies, e.g. including head and neck cancer, ovarian cancer, glioblastoma, pancreatic cancer, breast cancer, lung cancer, and colorectal cancer (see, e.g., Geethadevi A et al. ERBB signaling in CTCs of ovarian cancer and glioblastoma. Genes & Cancer 2017, 8:746-751; Sigismund S et al., Emerging functions of the EGFR in cancer. Molecular Oncol 2018, 12:3-20). It has therefore long represented an oncologic target of immense interest (Normanno N et al., *Epidermal growth factor receptor (EGFR) signaling in cancer*. Gene 2006, 366:2-16).

Existing therapeutic approaches for targeting EGFR involve monoclonal antibodies (mAb) and small molecule tyrosine kinase inhibitors (TKI). Despite their improved therapeutic efficacy in other malignancies, EGFR-specific mAb and TKI treatments have not been approved for ovarian cancer and glioblastoma, among others, due to the non-specific toxicities and lack of therapeutic improvement in clinical trials (Secord A A et al., *Phase II trial of cetuximab and carboplatin in relapsed platinum-sensitive ovarian cancer and evaluation of epidermal growth factor receptor expression: a Gynecologie Oncology Group study*. Gynecol Oncl, 2008, 108:493-499; Posadas E M et al., *A phase II and pharmacodynamic study of gefitinib in patients with refractory or recurrent epithelial ovarian cancer*. Cancer 2007, 109:1323-1330; Vergote I B et al., *Randomized phase III study of erlotinib versus observation in patients with no evidence of disease progression after first-line platin-based chemotherapy for ovarian carcinoma: a European Organisation for Research and Treatment of Cancer-Gynaecological Cancer Group, and Gynecologic Cancer Intergroup study*. J Clin Oncol 2014, 32:320-326; Neyns B et al., *Stratified phase II trial of cetuximab in patients with recurrent high-grade glioma*. Ann Oncol 2009, 20(9):1596-1603; Hasselbalch B et al., *Cetuximab, bevacizumab, and irinotecan for patients with primary glioblastoma and progression after radiation therapy and temozolomide: a phase II trial*. Neuro Oncol 2010, 12(5):508-516; Peereboom D M et al., *Phase II trial of erlotinib with temozolomide and radiation in patients with newly diagnosed glioblastoma multiforme*. J Neuro Oncol 2010, 98:93-99; Chakravarti A et al., *RTOG 0211: a phase 1/2 study of radiation therapy with concurrent gefitinib for newly diagnosed glioblastoma patients*. Int J Radiat Oncol Biol Phys 2013, 85:1206-1211).

Photoimmunotherapy (PIT) employs antibody-photosensitizer conjugate (photo-immunoconjugate, PIC) and harmless near-infrared light ($\lambda$=600-900 nm) to induce reactive oxygen species (ROS)-mediated (e.g., $^1O_2$, $O_2^{·-}$, $·OH$) tumor destruction while sparing normal tissues (van Dongen G A et al., *Photosensitizer-antibody conjugates for detection and therapy of cancer*. Adv Drug Deliv Rev 2004, 56:31-52; Mitsunaga M et al., *Cancer cell-selective in vivo near infrared photoimmunotherapy targeting specific membrane molecules*. Nat Med 2011, 17:1685-1691; Schmidt S et al., *Clinical use of photodynamic therapy in gynecologic tumor patients—antibody-targeted photodynamic laser therapy as a new oncologic treatment procedure*. Zentralbl Gynakol, 1992, 114:307-311; Mew D et al., *Photoimmunotherapy: treatment of animal tumors with tumor-specific monoclonal antibody-hematoporphyrin conjugates*. J Immunol 1983, 130:1473-1477). The fluorescence signal generated from the excited photosensitizers can also be used for optical imaging and fluorescence-guided surgery (FGS) of tumors (van Dam G M et al., *Intraoperative tumor-specific fluorescence imaging in ovarian cancer by folate receptor-alpha targeting: first in-human results*. Nat Med 2011, 17:1315-1319).

Since the introduction of PIT in the 1980s (Mew D et al., *Photoimmunotherapy: treatment of animal tumors with tumor-specific monoclonal antibody-hematoporphyrin conjugates*. J Immunol 1983, 130:1473-1477), there has recently been interest in using PIC in the treatment of some cancers. For example, photoactivation of trastzumab-IRDye-700DX conjugate showed tumor reduction in ovarian mouse model (Sato K et al., *Near infrared photoimmunotherapy in the treatment of disseminated peritoneal ovarian cancer*. Mol Cancer Ther 2015, 14:141-150). Enhanced therapeutic efficacy has also been reported using anti-EGFR antibody ($Z_{EGFR:03115}$-IR700DX) conjugate in subcutaneous glioma xenografts (Burley T A et al., *Near-infrared photoimmunotherapy targeting EGFR-Shedding new light on glioblastoma treatment*. Int J Cancer 2018, 142:2363-2374). In addition, several EGFR-targeted PICs (e.g., Cetuximab-IRDeye700 and Panitumumab-IRDye800) are currently in clinical trials for PIT or FGS (NCT02422979, NCT03384238).

A PIC system was previously developed that comprises of an FDA-approved anti-EGFR monoclonal antibody (cetuximab, Cet) and a clinically used benzoporphyrin derivative (BPD) photosensitizer to target cancer cells (Savellano M D, Hasan T, *Targeting cells that overexpress the epidermal growth factor receptor with polyethylene glycolated BPD verteporfin photosensitizer immunoconjugates*. Photochem Photobiol 2003, 77:431-439; Abu-Yousif A O et al., *Epidermal growth factor receptor-targeted photosensitizer selectively inhibits EGFR signaling and induces targeted photo-toxicity in ovarian cancer cells*. Cancer letters 2012, 321:

120-127; Inglut C T et al., *Systematic Evaluation of Light-Activatable Biohybrids for Anti-Glioma Photodynamic Therapy*. J Clin Med 2019, 8(9):1269; Huang H C et al., *Immobilization of Photo-Immunoconjugates on Nanoparticles Leads to Enhanced Light-Activated Biological Effects*. Small 2018:e1800236; Spring B Q et al., *Selective treatment and monitoring of disseminated cancer micrometastases in vivo using dual-function, activatable immunoconjugates*. Proc Natl Acad Sci USA 2014, 111(10):E933-E942). The highly self-quenched BPD photosensitizer molecules conjugated to Cet can be de-quenched (activated) by cancer cells via lysosomal proteolysis of the antibody (Savellano M D, Hasan T, *Targeting cells that overexpress the epidermal growth factor receptor with polyethylene glycolated BPD verteporfin photosensitizer immunoconjugates*. Photochem Photobiol 2003, 77:431-439; Huang H C et al., *Immobilization of Photo-Immunoconjugates on Nanoparticles Leads to Enhanced Light-Activated Biological Effects*. Small 2018: e1800236; Spring B Q et al., *Selective treatment and monitoring of disseminated cancer micrometastases in vivo using dual-function, activatable immunoconjugates*. Proc Natl Acad Sci USA, 2014, 111(10):E933-E942).

It has also been established that light activation of benzoporphyrin derivative (BPD) induces photochemical disruption of the mitochondrial membrane (Inglut C T et al., *Systematic Evaluation of Light-Activatable Biohybrids for Anti-Glioma Photodynamic Therapy*. J Clin Med 2019, 8(9):1269), which triggers the release of cytochrome c, a potent initiator of apoptotic cell death (Kessel D, Castelli M, *Evidence that bcl-2 is the target of three photosensitizers that induce a rapid apoptotic response*. Photochem Photobiol 2001, 74:318-322; Kessel D, Luo Y, *Mitochondrial photodamage and PDT-induced apoptosis*. J Photochem Photobiol B 1998, 42:89-95; Kessel D et al., *The role of subcellular localization in initiation of apoptosis by photodynamic therapy*. Photochem Photobiol 1997, 65:422-426). This shifts the balance in the target cells from an anti-apoptotic state to a more pro-apoptotic state, mediating eventual cell death.

While PIT leverages PIC to minimize damage to healthy tissues, it requires a threshold intracellular PIC concentration for effective tumor destruction (Inglut C T et al., *Systematic Evaluation of Light-Activatable Biohybrids for Anti-Glioma Photodynamic Therapy*. J Clin Med 2019, 8(9):1269; Spring B Q et al., *Selective treatment and monitoring of disseminated cancer micrometastases in vivo using dual-function, activatable immunoconjugates*. Proc Natl Acad Sci USA 2014, 111(10):E933-E942). Unfortunately, prior attempts to overcome insufficient PIC uptake have not been successful. One of the strategies to overcome the insufficient PIC uptake is to combine nanotechnology with PIC. With a high surface area-to-volume ratio, nanoparticles can be decorated with large amounts of antibodies for tumor targeting (Peer D et al., *Nanocarriers as an emerging platform for cancer therapy*. Nature Nanotechnology 2007, 2:751-760).

For many combinations to achieve optimal efficacy, spatiotemporal control of drug exposure to coordinate target inhibition of interconnected cancer survival and growth pathways is of paramount importance (Chabner B A, Roberts T G, Jr., *Timeline: Chemotherapy and the war on cancer*. Nat Rev Cancer 2005, 5:65-72; Lopez J S, Banerji U, *Combine and conquer: challenges for targeted therapy combinations in early phase trials*. Nat Rev Clin Oncol 2017, 14:57-66). In addition to targeting multiple survival pathways or blocking cell death escape mechanisms, drugs that are the best candidates for combination are those that target all major regions of a cell (i.e., plasma membrane, cytoplasm, and nucleus) and also have non-overlapping toxicities (Sakhrani N M, Padh H, *Organelle targeting: third level of drug targeting*. Drug design, development and therapy 2013, 7:585-599; Barua S, Mitragotri S, *Synergistic targeting of cell membrane, cytoplasm, and nucleus of cancer cells using rod-shaped nanoparticles*. ACS Nano 2013, 7:9558-9570).

With new analytical, optical, and biochemical tools being developed for advancing personalized medicine, there has been a surge in interest towards the development of smart nanoplatforms that precisely coordinate cancer cell exposure to multiple drugs, and thereby promote synergy and boost efficacy.

SUMMARY OF THE INVENTION

The present disclosure relates to photodynamic therapy systems and methods for spatiotemporal agent delivery. In some embodiments, the system is utilized for dynamic, multi-tier targeting of cancer and other diseases. The disclosed systems employ simultaneous delivery of multiple therapeutic agents. The co-delivered therapeutic agents may be molecularly distinct therapeutics, such that they target different cellular regions or mechanisms. In some embodiments, the system includes anti-cancer agents that target (bio) molecules in all major functional parts (the plasma membrane, cytoplasm and nucleus) of cancer cells. In some embodiments, the system includes photosensitizer conjugates, such that the delivered agents target desired regions and at desired times.

In some embodiments, the present invention is directed to a photo-immunoconjugate formulation, suitable for the treatment of cancer. The formulation comprises a nanoparticle carrier, a first therapeutic agent coupled to the nanoparticle carrier, a photosensitizer molecule coupled to the first therapeutic agent and/or the nanoparticle carrier, and a second therapeutic agent coupled to the first therapeutic agent and/or the nanoparticle carrier.

In some embodiments, the first therapeutic agent is an ATP-bind cassette (ABC) transporter inhibitor. In some implementations, the first therapeutic agent is an epidermal growth factor receptor (EGFR) inhibitor or a receptor tyrosine kinase inhibitor. In some embodiments, the first therapeutic agent is an antibody, an antigen-binding fragment thereof, or a diabody. In some implementations, the first therapeutic agent is cetuximab, panitumumab or trastuzumab. In some embodiments, the photosensitizer molecule is a benzoporphyrin derivative (BPD) photosensitizer, a chlorin-based photosensitizer, a porphyrin-based photosensitizer, a bacteriochlorin-based photosensitizer, a phthalocyanine-based photosensitizer, or a fluorescence imaging agent. In some embodiments, the second therapeutic agent is an anti-cancer agent, e.g., a chemotherapy agent. In some implementations, the chemotherapy agent is a topoisomerase inhibitor, e.g., irinotecan (IRI), topotecan, or camptothecin. However, it would be understood by one of skill in the art that various other therapeutic agents may be utilized as the first and/or second therapeutic agent(s), including but not limited to another anti-cancer agent, an antibacterial agent, an antibiotic agent, and antimicrobial agent, and/or an anti-inflammatory agent.

In some embodiments, the nanoparticle carrier is a liposome, a micelle, an organic nanoscale object, an inorganic nanoscale object, or a microparticle thereof. In some implementations, the first and/or second therapeutic agent is encapsulated within the nanoparticle carrier, e.g., within a liposome.

Formulations of the present disclosure may be provided as pharmaceutical compositions formulated with pharmaceutically acceptable carriers or diluents as well as any other known adjuvants and excipients in accordance with conventional techniques, e.g., such as those disclosed in Remington: *The Science and Practice of Pharmacy,* 21th Edition, Gennaro, Ed., Mack Publishing Co., Easton, PA, 2005. The pharmaceutically acceptable carriers or diluents, as well as any other known adjuvants and excipients, should be suitable for the chosen compounds of the present invention and the chosen mode of administration. A pharmaceutical composition of the present invention may thus include diluents, fillers, salts, buffers, detergents, stabilizers (e.g., sugars or protein-free amino acids), preservatives, tissue fixatives, solubilizers, and/or other materials suitable for inclusion in the composition. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The present invention is also directed to a method of enhancing photosensitizer delivery to a target, e.g., such as, for the treatment of a disease and/or as an imaging or detectable agent. In some implementations, the disclosed method comprises administering a therapeutically effective amount of the disclosed photo-immunoconjugate formulation(s) to a subject. As described above, the photo-immunoconjugate formulation comprises: a nanoparticle carrier; a first therapeutic agent coupled to said nanoparticle carrier; a photosensitizer molecule coupled to said first therapeutic agent and/or said nanoparticle carrier; a second therapeutic agent coupled to said first therapeutic agent and/or said nanoparticle carrier.

A "therapeutically effective amount" refers to the amount of the photo-immunoconjugate formulation sufficient to elicit a desired biological response in a subject, e.g., such as an amount sufficient to kill, reduce or stabilize cells associated with a disease or condition and/or sufficient to reduce symptoms associated with such disease or condition. Actual dosage levels of the active ingredient(s) in the disclosed formulations may be varied so as to obtain an amount of the active ingredient which is effective to achieve the desired therapeutic response for a particular patient, composition, and mode of administration. The formulations and compositions of the present invention may be administered by any suitable route and mode (e.g., parenteral, injected, topical, oral, intranasal, etc.).

In some embodiments, the present disclosure is directed to a method of treating cancer comprising administering a therapeutically effective amount of the disclosed photo-immunoconjugate formulation(s) to a patient in need thereof. As described above, the photo-immunoconjugate formulation thus comprises: a nanoparticle carrier; a first therapeutic agent coupled to said nanoparticle carrier; a photosensitizer molecule coupled to said first therapeutic agent and/or said nanoparticle carrier; a second therapeutic agent coupled to said first therapeutic agent and/or said nanoparticle carrier.

In some implementations, the disclosed formulations and methods are directed to the treatment of a cancer characterized by expression of EGFR. In some embodiments, disclosed formulations and methods are directed to the treatment of head and neck cancer, ovarian cancer, glioblastoma, pancreatic cancer, breast cancer, lung cancer, prostate cancer, bladder cancer, or colorectal cancer.

In some implementations, the disclosed methods provide for photoactivating the photosensitizer molecule of the disclosed formulations following administration thereof, e.g., such as for the treatment of cancer and/or another disease or condition, and/or as a detectable or imaging agent.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee.

FIG. 13. Immunoblotting of EGFR and γ-H2AX expressions in OVCAR-5 cells at 24 hours and 47 hours after incubation of PIC, Nal-IRI, and PIC-Nal-IRI. Whole cell extracts (40 μg) were loaded into each lane. β-Actin was used as a loading control. (a) Downregulation of EGFR was most pronounced when treated with PIC-Nal-IRI. (b) The γ-H2AX expression remained the same across different treatment group. (n=3; *P<0.05; P<0.01; *P<0.001; one-way ANOVA, Tukey's posthoc test).

DETAILED DESCRIPTION OF THE INVENTION

Figure 1:
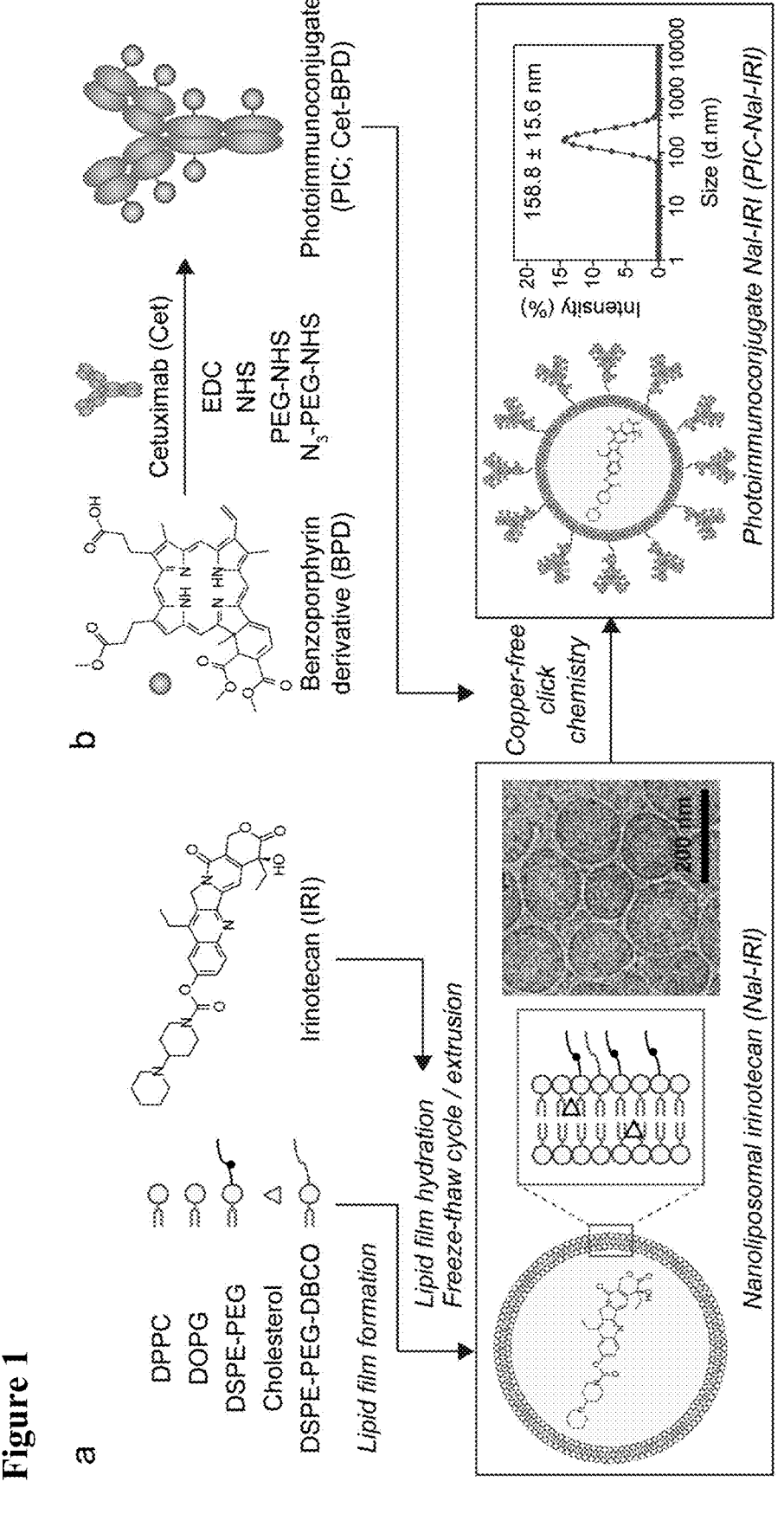
FIG. 1. Schematic diagram of the steps for photo-immunoconjugate nanoliposomal irinotecan (PIC-Nal-IRI) synthesis. (a) Synthesis and cryogenic electron microscopy image of monodispersed nanoliposomal irinotecan (Nal-IRI) with an average size of ~150 nm (PdI<0.1, n>3). (b) Benzoporphyrin derivative (BPD) was covalently conjugated onto cetuximab (Cet) via carbodiimide chemistry to form photo-immunoconjugate (PIC). Copper-free click chemistry was employed to tether PICs onto Nal-IRI to form PIC-Nal-IRI with an average size of 158.8±15.6 nm (PdI<0.1, n>3).

The most effective therapies for cancer often involve combination treatments that target multiple non-overlapping pathways while minimizing side effects. Significant efforts have been made to develop nanoparticle-mediated combination therapy that targets the same subcellular organelle to modulate the interconnected molecular pathways (J. Shi et al., *Cancer nanomedicine: progress, challenges and opportunities*, Nature Rev Cancer 2017, 17:20-37). Nanoparticle-mediated combination therapy is capable of delivering multiple anti-cancer agents to target, e.g., the plasma membrane, the cytoplasm, and the nucleus to elicit the drug efflux inhibition (J. Wu et al., *Reversal of multidrug resistance by transferrin-conjugated liposomes co-encapsulating doxorubicin and verapamil*, Journal of pharmacy & pharmaceutical sciences: a publication of the Canadian Society for Pharmaceutical Sciences, Societe canadienne des sciences pharmaceutiques 2007, 10:350-357; O. B. Garbuzenko et al., *Inhibition of lung tumor growth by complex pulmonary delivery of drugs with oligonucleotides as suppressors of cellular resistance*, Proc Natl Acad Sci USA 2010, 107: 10737-10742), gene silencing (G. Shim et al., *Trilysinoyl oleylamide-based cationic liposomes for systemic co-delivery of siRNA and an anticancer drug*, J Control Release 2011, 155:60-66; Y. Yang et al., *Nanoparticle delivery of pooled siRNA for effective treatment of non-small cell lung cancer*, Mol Pharm 2012, 9(8):2280-2289), or DNA damage (P. G. Tardi et al., *Drug ratio-dependent antitumor activity of irinotecan and cisplatin combinations in vitro and in vivo*, Mol Cancer Ther 2009, 8:2266-2275; G. Batist et al., *Safety, pharmacokinetics, and efficacy of CPX-1 liposome injection in patients with advanced solid tumors*, Clin Cancer Res 2009, 15(2):692-700). While multi-pathway targeting can induce enhanced cytotoxicity, multi-subcellular targeting of the delivered therapeutics should also be considered to expand the organelle-based apoptotic pathways (Sakhrani N M, Padh H, *Organelle targeting: third level of drug targeting*, Drug Des Devel Ther 2013, 7:585-599).

PIT involves targeted delivery of photosensitizers via an antibody conjugate (i.e., photo-immunoconjugate, PIC) followed by light activation for selective tumor killing. The trade-off between PIC selectivity and PIC uptake has been a major challenge and limited the efficacy of photoimmuno- therapy using conventional approaches. Despite evidence showing that photoimmunotherapy is most effective when combined with chemotherapy, the design of nanocarriers to co-deliver PIC and chemotherapy has heretofore remained an unmet need.

To overcome these challenges, the present disclosure provides for a novel photo-immunoconjugate-nanoliposome comprising multiple therapeutic agents. In some implemen- tations, nanocarrier formulations comprise three clinically used agents: anti-EGFR monoclonal antibody cetuximab (Cet), benzoporphyrin derivative (BPD) photosensitizer, and irinotecan (IRI) chemotherapy. Nanotechnology is com- bined with photochemistry to simultaneously deliver and sequentially activate multiple drugs that target distinct regions of a cancer cell, e.g., plasma membrane, cytoplasm, and nucleus. The disclosed platforms and techniques effec- tively overcome selectivity-uptake trade-off, improve pho- toimmunotherapy efficacy, and enable multi-tier cancer tar- geting. Controllable drug compartmentalization, easy surface modification, and high clinical relevance is achieved.

The initial goals of integrating nanotechnology and pho- todynamic therapy (PDT) were to enhance the solubility of hydrophobic photosensitizers in aqueous environment and increase the photosensitizer payload delivered to the cells (S. S. Lucky et al., *Nanoparticles in Photodynamic Therapy*, Chem Rev 2015, 115:1990-2042). Visudyne® is a benzo- porphyrin derivative (BPD)-based liposomal formulation approved by the FDA for age-related macular degeneration to improve delivery of BPD to neovasculature (R. K. Chow- dhary et al., *Drug release characteristics of lipid based benzoporphyrin derivative, Journal of pharmacy & phar- maceutical sciences: a publication of the Canadian Society for Pharmaceutical Sciences*, Societe canadienne des sci- ences pharmaceutiques 2003, 6:13-19). Porphyrin-inte- grated porphysomes were developed as biophotonic contrast agents and for in vivo photodynamic tumor ablation (J. F. Lovell et al., *Porphysome nanovesicles generated by por- phyrin bilayers for use as multimodal biophotonic contrast agents*, Nature Materials 2011, 10:324-332). The therapeutic efficacy of various BPD-anchored nanoliposomes has also been examined (G. Obaid et al., *Nanolipid Formulations of Benzoporphyrin Derivative: Exploring the Dependence of Nanoconstruct Photophysics and Photochemistry on Their Therapeutic Index in Ovarian Cancer Cells*, Photochem Photobiol 2019, 95:364-377).

In contrast to previous nanoformulations, the nanocarrier disclosed herein leverages PIT to introduce a secondary therapeutic modality, a therapeutic antibody, in addition to the conventional PDT. PIT utilizes antibody-photosensi- tizer-conjugates (PIC) for targeted PDT. The nanotechnol- ogy and nanoformulations disclosed herein is sometimes referred to herein as "nano-PIT". By using simple carbo- diimide chemistry and copper-free click chemistry, BPD molecules were tethered onto clinically-relevant cetuximab, an anti-EGFR monoclonal antibody. The resulting PICs were then conjugated onto nanoliposomes (Nal). Conjuga- tion chemistry did not alter the Q band (690 nm; excitation wavelength for PIT and nano-PIT) of BPD as neither con- jugation method reduces the number of double bonds in pyrrole group of BPD (H. Abrahamse, M. R. Hamblin, *New photosensitizers for photodynamic therapy*, Biochem J 2016, 473:347-364). Furthermore, photoactivity and singlet oxygen yield of BPD were enhanced after PIC immobiliza- tion onto the nanoliposomes due to the improved PIC stability upon nanoparticle conjugation (S. Puertas et al., *Designing novel nano-immunoassays: antibody orientation versus sensitivity*, J Phys D: Applied Physics 2010, 43:474012).

Immobilization of PICs onto nanoparticles overcomes the persistent challenge of insufficient intracellular photosensi- tizer accumulation, which is prevalent in conventional PIT delivery techniques (Huang H C et al., Immobilization of Photo-Immunoconjugates on Nanoparticles Leads to Enhanced Light-Activated Biological Effects, Small 2018, e1800236). We refer to this phenomenon as the 'carrier effect'. Using our current nano-PIT formulation, Photo- immunoconjugate-nanoliposome (PIC-Nal), we discovered that the 'carrier effect' depends on three important param- eters: i) the expression level of the target receptor, ii) physical size of the nanocarrier, and iii) antibody density of the nanocarrier. In the cellular uptake study, it was observed that PIC-Nal induced a higher intracellular BPD concentra- tion after 24 hours of incubation compared to conventional PIC incubation in high EGFR-expressing OVCAR-5 ovar- ian cancer cells; however, the opposite was true using low EGFR-expressing U87 glioblastoma cells. We hypothesized that such variation of the 'carrier effect' across different cell line is likely due to the difference in EGFR expression as cells with low EGFR expression provide less opportunity for the antibody-receptor binding event to occur as the number of EGF receptor is limited.

In addition to receptor dependency, the 'carrier effect' may also depend on the size of the nanocarrier. Using computational modeling, Gonzalez-Rodriguez et al. sug- gests that cytoplasmic rigidity limits internalization of larger particles with radii above the optimal radius of 50 nm via receptor-mediated endocytosis (D. Gonzalez-Rodriguez, A. I. Barakat, Dynamics of receptor-mediated nanoparticle internalization into endothelial cells, PLOS One 2015, 10:e0122097). Larger particles can induce steric hindrance as binding of one relatively large particle may block nearby and otherwise available receptors for binding in a receptor- scarce environment. Furthermore, antibody density and binding affinity of the antibody on the nanocarrier are also factors for effective internalization. Vácha et al. observed an increase in receptor-mediated endocytosis with increasing ligand coverage on the nanoparticles or increasing binding affinity of the ligand to the receptor via computer stimulation (R. Vácha et al., *Receptor-Mediated Endocytosis of Nan- oparticles of Various Shapes*, Nano Lett 2011, 11:5391- 5395). Based on the present studies, it appears that the 'carrier effect' phenomenon not only depends on the target receptor expression, but also relies on the size, antibody density, and ligand affinity of the nanoconstruct.

In addition to enhancing the therapeutic effect of PIT, covalent conjugation of PICs on nanoliposomes allows for the incorporation of high payloads of another therapeutic agent inside the aqueous liposome core. Irinotecan was incorporated as the third therapeutic agent in nano-PIT to induce DNA damage within the nucleus at a fixed PIC: irinotecan molar ratio of 1:7. It was observed that irinotecan loaded PIC-Nal (PIC-Nal-IRI) elicited synergistic cytotox- icity (48 hours drug-light interval) when compared to mono- therapy of PIC and liposomal irinotecan (Nal-IRI) under the same experimental conditions in OVCAR-5 and U87 cells. PIC-Nal-IRI exhibited higher cell cytotoxicity compared to the unconjugated mixture (PIC+Nal-IRI) in OVCAR-5 cells but not in U87 cells. This is believed to be due to the lack of 'carrier effect' previously observed.

It is increasingly evident that therapeutic synergy of combination treatment depends in part on the delivery of the desired drug molar ratio to the tumor because of the dissimilar pharmacokinetics of the individual agent (J. Jia et al., Mechanisms of drug combinations: interaction and network perspectives. Nat Rev Drug Discov 2009, 8(2):111-128). CPX-351 (CombiPlex®) is a liposomal formulation that co-encapsulate cytarabine and daunorubicin at a fixed synergistic molar ratio that was recently approved the FDA as a combination treatment for acute myeloid leukemia (AML) (E. J. Feldman et al., *First-in-man study of CPX-351: a liposomal carrier containing cytarabine and daunorubicin in a fixed* 5:1 *molar ratio for the treatment of relapsed and refractory acute myeloid leukemia*, J Clin Oncol 2011, 29(8):979-985).

In accordance with the present disclosure, an intelligently designed nanoliposome formulation is provided that targets multiple cellular regions using three mechanistically distinct therapeutic agents at fixed molar ratio: i) cetuximab modulation of membrane EGF receptor, ii) PIT-induced mitochondrial membrane depolarization, and iii) inhibition of DNA replication via irinotecan. The disclosed PIC-Nal-IRI formulations overcome the inherent uptake difficulties of conventional multi-drug delivery systems. Furthermore, therapeutic efficacy is substantially enhanced by targeting different major components of the cancer cell. The uniqueness of PIC-Nal-IRI lies in part in the dynamic molecular modulation of the multi-tier cell targeting. Cancer cells employ different molecular mechanisms to evade apoptosis by upregulating cell survival pathways while disabling apoptotic pathways (K. Fernald, M. Kurokawa, *Evading apoptosis in cancer*, Trends Cell Biol 2013, 23(12):620-633).

It is therefore advantageous for combination treatment to target different major cellular components to elicit different stages of apoptosis. Three mechanistically distinct therapeutics, cetuximab, BPD, and irinotecan, were integrated into nano-PIT to target the plasma membrane, the mitochondria, and the nucleus, respectively. The simultaneous co-delivery of cetuximab and irinotecan abrogated EGFR expression and enhanced DNA damage respectively within 24 hours of administration. Subsequent photoactivation of BPD after 48 hours degraded anti-apoptotic protein Bcl-2 to enhance the cytotoxicity. The disclosed nano-PIT system is efficacious as a neoadjuvant therapy to reduce the size of the primary tumor, and as an adjuvant to surgery with initial de-bulking followed by photoactivation of nano-PIT to eliminate residual cancer cells.

In this study, the generalizability of the 'carrier effect' is demonstrated using a novel PIC-Nal formulation. Furthermore, the PIC-Nal is rationally designed to co-deliver irinotecan chemotherapy for enhanced PIT outcomes. Nanoliposomal irinotecan injection (Onivyde®, Nal-IRI) is a valuable chemotherapy given in combination with fluorouracil and leucovorin to patients with gemcitabine-refractory metastatic pancreatic cancer, and it is now being tested in patients with gastric adenocarcinoma (NCT03739801), gynecological cancer (NCT01770353), lung cancer (NCT03088813), and glioblastoma (NCT03119064) (Vredenburgh J J et al., *Experience with irinotecan for the treatment of malignant glioma*. Neuro-Oncology 2009, 11:80-91; Pommier Y, *Topoisomerase I inhibitors: camptothecins and beyond*. Nat Rev Cancer 2006, 6:789-802; Herrlinger U et al., *Bevacizumab Plus Irinotecan Versus Temozolomide in Newly Diagnosed O6-Methylguanine-*

*DNA Methyltransferase Nonmethylated Glioblastoma: The Randomized GLARIUS Trial*. J Clin Oncol 2016, 34:1611-1619; Saif M W, *MM-398 achieves primary endpoint of overall survival in phase III study in patients with gemcitabine refractory metastatic pancreatic cancer*. Jop 2014, 15:278-279).

Irinotecan acts by inhibiting topoisomerase I (Top1) and trapping Top1-DNA cleavage complexes (Top1cc) to induce double-stranded DNA breaks in the nucleus and promote direct cell death (Parchment R E, Pessina A, Topoisomerase I inhibitors and drug resistance. Cytotechnology 1998, 27:149-164). It has been shown that light activation of nanoliposomal BPD (photodynamic therapy, PDT) synergizes with irinotecan to improve survival outcomes in pancreatic cancer mouse models (Huang H C et al., Photodynamic Priming Mitigates Chemotherapeutic Selection Pressures and Improves Drug Delivery. Cancer Res 2018, 78:558-571; Huang H C et al., Photodynamic Therapy Synergizes with Irinotecan to Overcome Compensatory Mechanisms and Improve Treatment Outcomes in Pancreatic Cancer. Cancer Res 2016, 76:1066-1077; Pigula M et al., Size-dependent Tumor Response to Photodynamic Therapy and Irinotecan Monotherapies Revealed by Longitudinal Ultrasound Monitoring in an Orthotopic Pancreatic Cancer Model. Photochem Photobiol 2019, 95(1):378-386). It has also been demonstrated that light activation of irinotecan-loaded porphysomes reduces pancreatic tumor burden (Carter K A et al., Sphingomyelin Liposomes Containing Porphyrin-phospholipid for Irinotecan Chemophototherapy. Theranostics 2016, 6:2329-2336). However, all of these prior studies utilized non-targeted nanoliposomes carrying unquenched photosensitizers that are at a higher risk of normal tissue phototoxicity.

The disclosed combination therapy targets multiple cellular components for enhanced therapeutic synergy. In accordance with the disclosed embodiments, a photo-immunoconjugate nanoplatform is provided that simultaneously delivers three regimens in a unique manner—where a therapeutic antibody (e.g., cetuximab) selectively targets the membrane-bound epidermal growth factor receptor (EGFR) for effective photodynamic depolarization of cytosolic mitochondria using light-activatable benzoporphyrin derivative (BPD) photosensitizers, and the subsequent release of topoisomerase inhibitor (irinotecan) induces potent nuclear DNA damage for synergistic outcomes. It is demonstrated that click chemistry coupling of photo-immunoconjugates (BPD-cetuximab) onto irinotecan-loaded nanoliposomes markedly enhances intracellular BPD delivery and potentiates photoimmunotherapy in EGFR-high ovarian cancer cells, but not in EGFR-low glioblastoma cells. In addition, this confirms that click conjugation of PIC onto Nal does not impair PIC's ability to inhibit EGFR. Despite this diminished 'carrier effect' in EGFR-low cancers, the combination of photoimmunotherapy with irinotecan synergistically reduced the cell viability in two exemplary cancer lines (CI<0.2-0.8). Controllable drug compartmentalization, easy surface modification, and high clinical relevance collectively make the photo-immunoconjugate nanoplatform extremely valuable.

The present invention relates to hybrid nanocarriers, e.g. based on PIC and nanoliposome, for combination therapy. The nanocarriers may be readily designed to compartmentalize multiple agents at a fixed ratio, target deliver therapeutics to cancer cells at a high payload, and generate cytotoxic ROS upon light activation (Huang H C, Hasan T, The "Nano" World in Photodynamic Therapy. Austin J Nanomed Nanotechnol 2014, 2(3):1020).

In some implementations, a tumor-activatable PIC system (Cet-BPD) (Savellano M D, Hasan T, *Targeting cells that overexpress the epidermal growth factor receptor with polyethylene glycolated BPD verteporfin photosensitizer immunoconjugates.* Photochem Photobiol 2003, 77:431-439; Inglut C T et al., *Systematic Evaluation of Light-Activatable Biohybrids for Anti-Glioma Photodynamic Therapy.* J Clin Med 2019, 8(9):1269) is leveraged to improve the selectivity and efficacy of irinotecan. PIC and nanoliposomal irinotecan are interfaced for targeted photoimmuno-chemotherapy. As compared to monotherapies, the mechanism-based nanotechnology disclosed herein, e.g., comprising Cet, BPD, and irinotecan, is much more effective in reducing cancer viability by targeting multiple subcellular components and molecular pathways. In addition, the disclosed platform exhibits enhanced PIC uptake, a major challenge in PIT as noted above.

BPD was first tethered to Cet at various molar ratios using carbodiimide chemistry to form PIC. Conjugation of PICs onto nanoliposome irinotecan (Nal-IRI) was then facilitated by copper-free click chemistry (FIG. 1), which resulted in monodispersed PIC-Nal-IRI constructs with an average size of 158.8±15.6 nm. As demonstrated herein, the disclosed PIC-Nal-IRI constructs are highly selective against EGFR-overexpressing epithelial ovarian cancer cells with 2-fold to 6-fold less accumulation in low EGFR expressing cells. The successful coupling of PIC onto Nal-IRI enhanced PIC uptake and photoimmunotherapy efficacy by up to 30% in OVCAR-5 cells. Furthermore, PIC-Nal-IRI synergistically reduced cancer viability via a unique three-way mechanism—EGFR downregulation, mitochondrial depolarization, and DNA damage.

Additional characteristics and features of the present disclosure will be further understood through reference to the following additional examples and discussion, which are provided by way of further illustration and are not intended to be limiting of the present disclosure.

Materials and Methods

Photo-Immunoconjugate (PIC) Synthesis and Characterization

Conjugation of BPD and chimeric anti-EGFR monoclonal antibody, cetuximab (Cet), was achieved via carbodiimide chemistry (Inglut C T et al., *Systematic Evaluation of Light-Activatable Biohybrids for Anti-Glioma Photodynamic Therapy.* J Clin Med 2019, 8(9):1269; Huang H C et al., *Immobilization of Photo-Immunoconjugates on Nanoparticles Leads to Enhanced Light-Activated Biological Effects.* Small 2018:e1800236). Briefly, Cet (152 kDa; 2 mg/mL) was pegylated with mPEG-NHS (40 kDa; 16 mg/mL) overnight at 400 RPM at room temperature. Pegylated Cet was mixed with BPD N-hydroxysuccinimidyl ester (BPD-NHS) and azide-PEG4-N-hydroxysuccinimidyl ester (azide-PEG-NHS) at 1:3:2.5 (Cet:BPD-NHS:azide-PEG-NHS), 1:6:2.5 (Cet:BPD-NHS:azide-PEG-NHS), and 1:9:2.5 (Cet:BPD-NHS:azide-PEG-NHS) molar ratios with constant stirring at 300 RPM for 20 hours at room temperature to create PIC. The resulting PIC was purified using a 7 kDa MWCO ZEBA™ spin desalting column that was pre-equilibrated with 30% DMSO in phosphate-buffered saline (PBS), and then concentrated with Amicon 30 kDa centrifugal filter tube.

Figure 2:
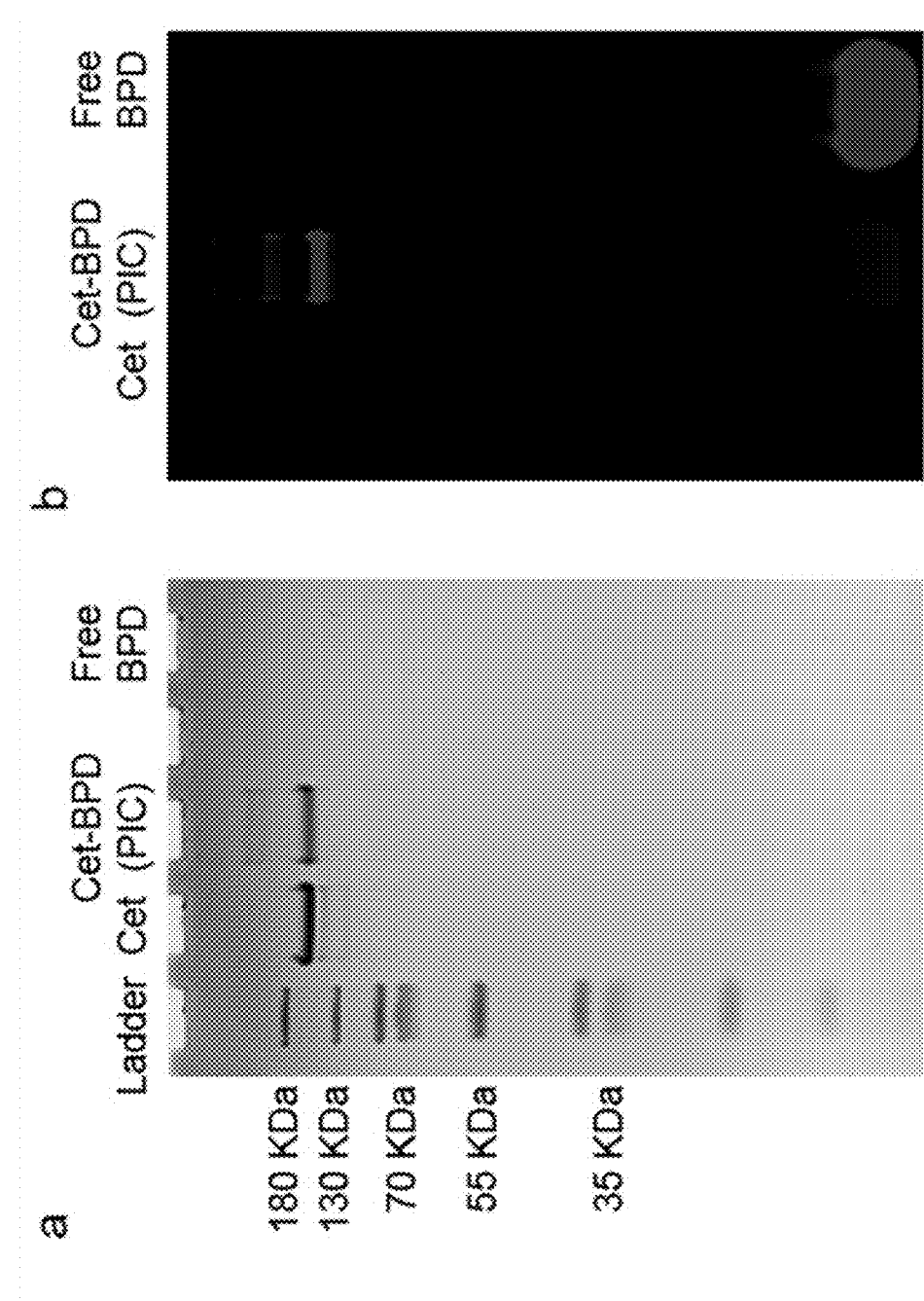
FIG. 2. The purity of Cet-BPD was assessed by gel fluorescence imaging analysis following sodium dodecyl sulfate polyacrylamide gel electrophoresis (SDS-PAGE). (a) Coomassie blue staining of SDS-PAGE for visualization of the standards (Ladder), Cet, Cet-BPD (PIC), and BPD. (b) Gel fluorescence imaging (Em: 690 nm) of SDS-PAGE shows <1% free BPD impurity in PIC; fluorescence intensity was quantified using ImageJ.

The purified PICs were then characterized using sodium dodecyl sulfate polyacrylamide gel electrophoresis and fluorescence gel analysis. BPD concentration in PICs was determined by absorbance in DMSO using established molar extinction coefficient, 80500 $M^{-1}cm^{-1}$ at 435 nm and 34,895 $M^{-1}cm^{-1}$ at 687 nm. The purity of PIC was confirmed to be over 99% using SDS-PAGE (FIG. 2). BPD concentration was determined by UV-Vis spectroscopy using established molar extinction coefficient (Table 1). Antibody concentration was determined using BCA assay.

TABLE 1

Molar Extinction Coefficients (E) And Equations For Determining Irinotecan Concentration (CIRI) And BPD Concentration (CBPD) Of PIC-Nal-IRI In DMSO Using Beer-Lambert Law.

| Absorbance (Abs., nm) | 367 nm | 348 nm | 435 nm | 687 nm |
|---|---|---|---|---|
| Irinotecan, $\varepsilon_{IRI}$ ($M^{-1}$ $cm^{-1}$) | 21,484 | 24,473 | 0 | 0 |
| BPD, $\varepsilon_{BPD}$ ($M^{-1}$ $cm^{-1}$) | 35,759 | 36,726 | 80,500 | 34,895 |

$$C_{IRI} = \left[ \frac{(Abs_{367} - Abs_{435})}{\varepsilon_{IRI@367} \times l} \times \frac{\varepsilon_{BPD@367}}{\varepsilon_{BPD@435}} + \frac{(Abs_{384} - Abs_{435})}{\varepsilon_{IRI@384} \times l} \times \frac{\varepsilon_{BPD@384}}{\varepsilon_{BPD@435}} \right] \times \frac{1}{2}$$

$$C_{BPD} = \left[ \frac{Abs_{435}}{\varepsilon_{BPD@435} \times l} + \frac{Abs_{687}}{\varepsilon_{BPD@687} \times l} \right] \times \frac{1}{2}$$

Nanoliposome Synthesis and Characterization

Nanoliposome (Nal) and nanoliposomal irinotecan (Nal-IRI) were prepared following freeze-thaw extrusion method (Huang H C et al., *Photodynamic Priming Mitigates Chemotherapeutic Selection Pressures and Improves Drug Delivery.* Cancer Res 2018, 78:558-571; Huang H C et al., *Photodynamic Therapy Synergizes with Irinotecan to Overcome Compensatory Mechanisms and Improve Treatment Outcomes in Pancreatic Cancer.* Cancer Res 2016, 76:1066-1077; Huang H C et al., *Mechanism-informed Repurposing of Minocycline Overcomes Resistance to Topoisomerase Inhibition for Peritoneal Carcinomatosis.* Mol Cancer Ther 2018, 17:508-520; Inglut C T et al., *Predictors and Limitations of the Penetration Depth of Photodynamic Effects in the Rodent Brain.* Photochem Photobiol, 2020, 96(2):301-309). Briefly, cholesterol, dipalmitoylphosphatidylcholine (DPPC), distearoyl-phosphatidylethanolamine-methoxy polyethylene glycol (DSPE-mPEG2000), distearoyl-glycerophosphoethanolamine-N-dibenzocyclooctyl polyethylene glycol (DSPE-mPEG2000-DBCO), and dioleoylglycerophosphoglycerol (DOPG; Avanti) were mixed at a molar ratio of 2.8:6:0.4:0.2:0.6, respectively. For selectivity and uptake studies, 0.1 mole % of dipalmitoylglycero-phosphoethanolamine-N-(lissamine Rhodamine B sulfonyl) (16:0 Liss Rhod PE) was added to the lipid film.

The resulting dried lipid film was hydrated with deionized water (1 mL) with or without irinotecan (3 mM) prior to freeze-thaw cycling (4-45° C.). Multi-laminar nanoliposomes were then extruded through polycarbonate membrane (Whatman; 0.1 µm pore size) at 45° C. and dialyzed against PBS to remove free irinotecan molecules. Zetasizer NanoZS (Malvern) was used to determine the size and zeta potential of the nanoliposomes. The concentration of irinotecan was determined using UV-Vis spectroscopy and established molar extinction coefficient of 20985 $M^{-1}cm^{-1}$ at 380 nm (Table 1) (Huang H C et al., *Photodynamic Priming Mitigates Chemotherapeutic Selection Pressures and Improves Drug Delivery.* Cancer Res 2018, 78:558-571; Huang H C et al., *Photodynamic Therapy Synergizes with Irinotecan to Overcome Compensatory Mechanisms and Improve Treatment Outcomes in Pancreatic Cancer.* Cancer Res 2016, 76:1066-1077; Huang H C et al., *Mechanism-informed Repurposing of Minocycline Overcomes Resistance to Topoisomerase Inhibition for Peritoneal Carcinomatosis.* Mol Cancer Ther 2018, 17:508-520). Entrapment efficacy of irinotecan was determined by the molar ratio of drug entrapped in liposomes to the total drug initially added.

Photo-Immunoconjugate-Nanoliposome Synthesis and Characterization

Photo-immunoconjugate-nanoliposomes (PIC-Nal) and photo-immunoconjugate-nanoliposomal irinotecan (PIC-Nal-IRI) were synthesized via cooper-free click chemistry (FIG. 1). Briefly, azide-containing PICs were mixed overnight with DBCO-containing Nal (or DBCO-containing Nal-IRI) at 60:1 ratio. Sepharose CL-4B size exclusion chromatography was used to purify PIC-Nal and PIC-Nal-IRI. Irinotecan and BPD concentrations were determined by UV-Vis spectroscopy and established molar extinction coefficients: 20985 $M^{-1}cm^{-1}$ at 380 nm for irinotecan, 80500 $M^{-1}cm^{-1}$ at 435 nm and 34,895 $M^{-1}$ $cm^{-1}$ at 687 nm for BPD (Table 1). Conjugation efficacy was determined by the molar ratio of PIC onto the liposomes to the total PIC added initially. Singlet oxygen sensor green (SOSG, 5 μM) was used to detect singlet oxygen ($^1O_2$) yield upon light irradiation of PIC-Nal-IRI or controls. BPD concentration is fixed at 5 μM. A microplate reader (BioTek) was used to acquire SOSG fluorescence signals (Ex/Em: 504/525 nm) before and after light irradiation (690 nm, 150 mW/cm², 20 J/cm²). Photoactivity is defined as the maximal fluorescence intensity (FI) of photosensitizer in PBS divided by the maximal FI of photosensitizer in DMSO.

The stability of the nanoformulations in PBS was determined by monitoring their hydrodynamic size and polydispersity index (PdI) over time. Irinotecan release from Nal-IRI and PIC-Nal-IRI was studied in 1% human serum at 37° C. under constant stirring using a dialysis setup described previously (Huang H C et al., *Photodynamic Priming Mitigates Chemotherapeutic Selection Pressures and Improves Drug Delivery*. Cancer Res 2018, 78:558-571; Huang H C et al., *Photodynamic Therapy Synergizes with Irinotecan to Overcome Compensatory Mechanisms and Improve Treatment Outcomes in Pancreatic Cancer*. Cancer Res 2016, 76:1066-1077).

Selectivity, Uptake, and Phototoxicity of PIC-Nal

Human ovarian cancer (OVCAR-5), human glioma (U87), and murine macrophage (J774) cell lines were purchased from ATCC and cultured in a 37° C., 5% CO₂ incubator with designated media (Roswell Park Memorial Institute medium for OVCAR5, Eagle's Minimum Essential Medium for U87, and Dulbecco's Modified Eagle's medium for J774). Cells were confirmed to be free of mycoplasma. For selectivity studies, EGFR(+) OVCAR-5 cells or EGFR (−) J774 cells were plated and grown overnight in 35-mm petri dish at 400 k cells per dish. Cells were incubated with rhodamine-labeled PIC-Nal (or rhodamine-labeled Nal) at a fixed rhodamine concentration (0.5 μM) for 30 minutes (37° C.). After incubation, cells were washed twice with PBS and dissolved in Solvable™. The rhodamine fluorescence signals (Ex/Em: 545/610 nm) were acquired using a microplate reader to determine the selective binding of PIC-Nal.

For uptake and phototoxicity studies, OVCAR-5 cells (200 k cells/35-mm dish) were incubated with PIC-Nal or controls (i.e., PIC alone, no-treatment) at a fixed BPD concentration (0.25 μM) for 24 hours. For uptake study, cells were washed twice with PBS and dissolved in SOLV-ABLE™. The BPD fluorescence signals (Ex/Em: 435/690 nm) were acquired using a microplate reader to quantify the uptake of PIC-Nal. In another set of experiments, washed cells were fixed with 4% paraformaldehyde, and stained with DAPI. Cells were imaged with the LionHeart Imager (BioTek) using the 10× objective to visualize the BPD signal (Ex/Em: 422/690 nm) and the DAPI signal (Ex/Em: 358/461 nm). BPD fluorescence intensity was quantified using ImageJ (Schneider C A et al., NIH Image to ImageJ: 25 years of image analysis. Nat Methods 2012, 9:671-675). For phototoxicity studies, cells were irradiated with a 690 nm laser (20 J/cm², 150 mW/cm²) at 24 hours post-incubation of PIC-Nal or controls. Cell viability was determined by MTT (3-(4,5-dimethylthiazol-2-yl)-2,5-diphenyltetrazolium bromide) assay (Thermo) at 24 hours post-light activation.

Photoimmuno-Chemotherapy Efficacy

To assess photoimmuno-chemotherapy efficacy, OVCAR-5 (5 k cells/well) and U87 cells (7 k cells/well), cultured in black-wall flat bottom 96-well plates, were incubated with PIC-Nal-IRI or controls at fixed drug concentrations (1 μM of BPD and 7 μM of irinotecan) for 48 hours prior to light activation (690 nm, 0-0.6 J/cm², 10 mW/cm²; Modulight). Cell viability was determined by MTT assay at 24 hours post-light activation. Mitochondrial membrane potential (ΔΨm) was examined via TMRE assay (Abcam). For western blot analyses, cell lysates (40 μg) were separated on 4-12% precast Bis-Tris protein gels and transferred onto a PVDF membrane. Subsequent to blocking with 5% BSA or milk in TBST solution, proteins were further detected using antibodies against EGFR(1:1000, Cell Signaling #2239) and γ-H2AX (1:500, EMP #05636). Anti β-actin antibodies (1:5000, Cell Signaling #3700) were used for the loading control. Visualization of protein bands was developed via chemiluminescence (SuperSignal) with exposure to a Gel Imager (ProteinSimple).

Statistical Analysis

All experiments were carried out at least in triplicate. Specific tests and number of repeats are indicated in the figure captions. Results are shown with mean±standard error of the mean (SEM). Statistical analyses were performed using GraphPad Prism (GraphPad Software). Synergistic effect of PIC-Nal-IRI was determined by using CompuSyn (CompoSyn Inc.) under non-constant ratio combo conditions comparing PIC, Nal-IRI, and PIC-Nal-IRI.

Results and Discussion

Synthesis and Characterization of PIC-Nal and PIC-Nal-IRI

For nanoliposome syntheses, Nal Nal-IRI with lipid compositions of cholesterol, dipalmitoylphosphatidylcholine, and distearoylphosphatidylethanolamine-methoxy polyethylene glycol were prepared using conventional lipid film hydration and extrusion through polycarbonate membrane. (FIG. 1). Nal and Nal-IRI were grafted with 4.5 mol % of polyethylene glycol, functionalized with 0.25 mol % of N-dibenzocyclooctyl (DBCO) and formed in size of 126.5±3.5 nm and 151.0±11.7 nm in diameter, respectively, with narrow size distribution (polydispersity index, PdI<0.1) (Table 2). To minimize the non-specific electrostatic interactions with cell membrane and maximize the contribution of specific interactions to binding and internalization (Wonder E et al., *Competition of charge-mediated and specific binding by peptide-tagged cationic liposome-DNA nanoparticles in vitro and in vivo*. Biomaterials 2018, 166:52-63; Miller C R et al., *Liposome-cell interactions in vitro: effect of liposome surface charge on the binding and endocytosis of conventional and sterically stabilized liposomes*. Biochemistry 1998, 37:12875-12883) the surface charge of nanoformulations was engineered to be neutral to slightly negative (between −13 mV and −19 mV; Table 2) by incorporating 6.9 mol % of dioleoylglycerophosphoglycerol (DOPG) into the lipid composition.

TABLE 2

Physical characterization of Sample Nanoformulations.

| Sample | Size (d. nm) | PdI | Zeta potential (mV) | Irinotecan Encapsulation Efficiency (%)* | PIC Conjugation Efficiency (%)** | Number of PIC per Nal |
|---|---|---|---|---|---|---|
| Nal | 126.5 ± 3.5 | 0.08 ± 0.01 | −19.6 ± 0.7 | N/A | N/A | N/A |
| PIC-Nal | 142.5 ± 5.9 | 0.06 ± 0.01 | −13.6 ± 0.6 | N/A | 66.5 ± 2.3 | 39.9 ± 1.4 |
| Nal-IRI | 151.0 ± 11.7 | 0.08 ± 0.01 | −16.6 ± 0.4 | 38.8 ± 4.4 | N/A | N/A |
| PIC-Nal-IRI | 158.8 ± 15.6 | 0.09 ± 0.03 | −14.8 ± 0.3 | 23.7 ± 2.2 | 48.0 ± 2.7 | 32.6 ± 2.6 |

*Encapsulation Efficiency (%): The molar ratio of irinotecan within the liposome after purification to that added initially.
**Conjugation Efficiency (%): The molar ratio of PIC conjugated onto the liposomal construct to that added initially.
Abbreviations: Nanoliposome (Nal); photo-immunoconjugate-nanoliposome (PIC-Nal); nanoliposomal irinotecan (Nal-IRI); photo-immunoconjugate-nanoliposomal irinotecan (PIC-Nal-IRI)

Figure 3:
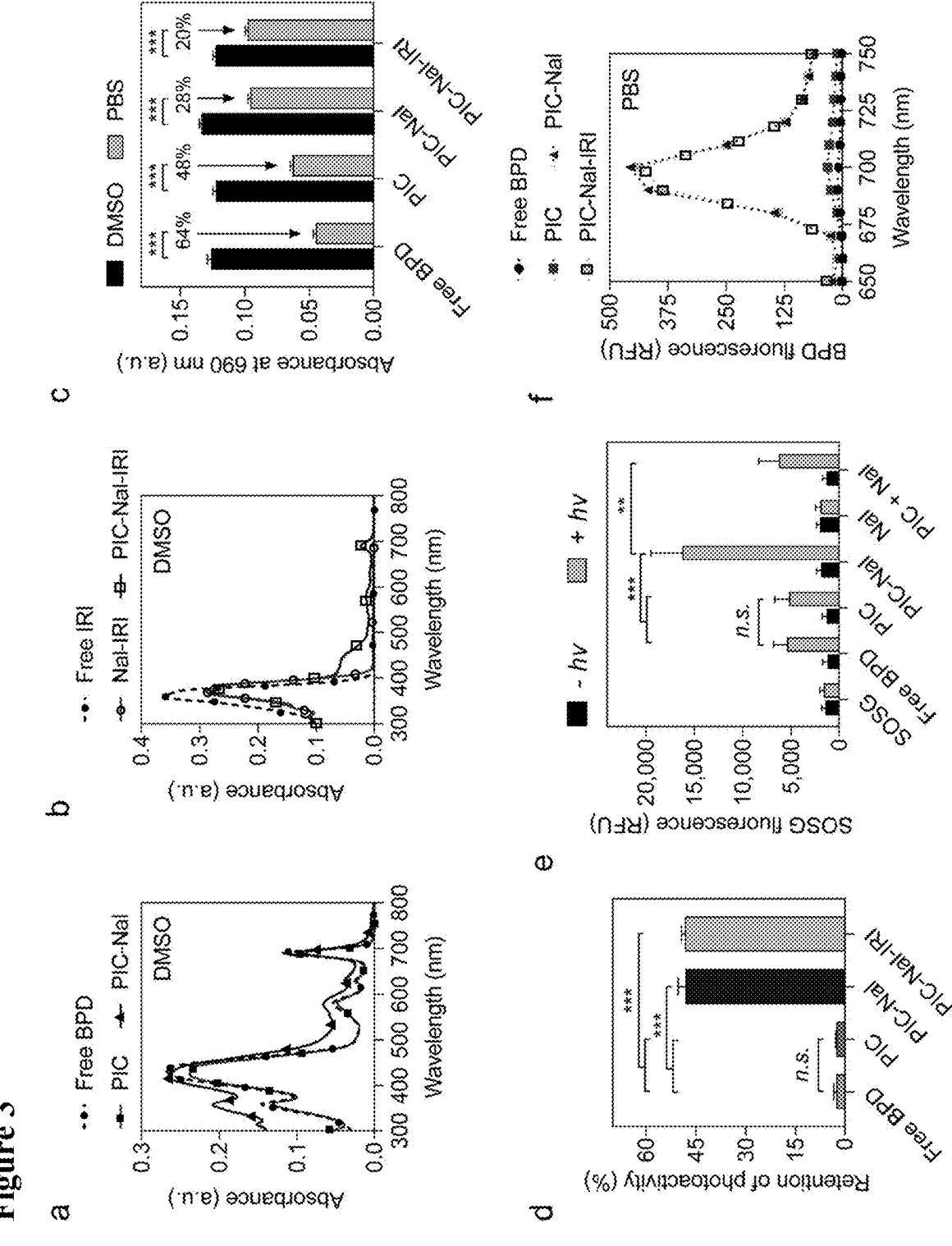
FIG. 3. Photophysical and Photochemical Characterizations of PIC, PIC-Nal, and PIC-Nal-IRI. (a) Absorbance spectra of BPD, PIC, and PIC-Nal in dimethyl sulfoxide (DMSO) showing overlapping main peaks centered at 435 nm (Soret band) and 690 nm (Q band; wavelength for light activation). (b) Absorbance spectra of irinotecan (IRI), Nal-IRI, and PIC-Nal-IRI in DMSO. (c) A comparison of the 690 nm absorbance value of BPD, PIC, PIC-Nal, and PIC-Nal-IRI in DMSO and PBS at a fixed BPD concentration. (d) Photoactivity of BPD, PIC, PIC-Nal, and PIC-Nal-IRI. (e) Singlet oxygen sensor green (SOSG) reports $^1O_2$ production from free BPD, PIC, PIC-Nal, Nal, and 'PIC+Nal' in PBS with and without light activation at 690 nm. (n>3;  p<0.01, * p<0.001; n.s.: non-significant; one-way ANOVA, Tukey's posthoc test). (f) Fluorescence spectra of BPD, PIC, PIC-Nal, and PIC-Nal-IRI in PBS.

PICs of varying BPD and cetuximab (Cet) molar ratios were prepared using carbodiimide chemistry (FIG. 1). Overnight reaction of BPD-NHS and Cet at 3:1, 6:1, and 9:1 molar ratio resulted in the formation of PICs with ~2, 4, and 6 BPD molecules per Cet, respectively. This corresponds to ~67% conjugation efficiency (Table 3). The apparent increase in measured hydrodynamic size compared to Nal-IRI and PIC-Nal-IRI is likely due to the presence of PICs, which are monoclonal antibody with an average size range of 5-6 nm (A. Hawe et al., *Taylor dispersion analysis compared to dynamic light scattering for the size analysis of therapeutic peptides and proteins and their aggregates.* Pharm Res 2011, 28(9):2302-2310). The surface charge of PIC-Nal-IRI was engineered to be neutral-to-slightly negative (−14.8±0.3 mV) by incorporating 6.86% of dioleoylglycerophosphoglycerol. The encapsulation efficiency and conjugation efficiency of the nanoliposomes were determined based on their respective UV-Vis absorbance spectra in dimethyl sulfoxide (DMSO) (FIG. 3a,b). Click chemistry conjugation of azide-functionalized PICs to DBCO-containing Nal or DBCO-containing Nal-IRI resulted in the formation of PIC-Nal and PIC-Nal-IRI with diameters of 142.5±5.9 nm and 158.8±15.6 nm, respectively (PdI<0.1) (Table 2). The conjugation efficiency of PIC to Nal was ~66% (Table 2), which corresponds to ~40 PICs per Nal. Increasing the BPD-to-Cet ratio of PIC did not significantly alter the size, surface charge, and conjugation efficiency of the PIC-Nal (Table 4).

TABLE 3

Synthesis of Photo-Immunoconjugates With Different BPD-to-Cetuximab (BPD:Cet) Ratio

| Stoichiometric Molar Ratio (BPD:Cet) | Final Molar Ratio (BPD:Cet) | Conjugation Efficiency (%)* |
|---|---|---|
| 9:1 | 6.13 ± 0.43 | 68.1 ± 1.54% |
| 6:1 | 3.87 ± 0.35 | 64.5 ± 1.01% |
| 3:1 | 2.04 ± 0.24 | 68.0 ± 0.96% |

*Conjugation Efficiency (%): The molar ratio of BPD conjugated onto Cet to that added initially.

TABLE 4

Physical Characterization Of Nanoliposome (Nal) and Photo-Immunoconjugate-Nanoliposomes (PIic-Nal) With Varying Bpd:Cet Ratio of Pic.

| Formulation (BPD:Cet) | Size (d) (nm) | PdI | Zeta potential (mV) | Conjugation Efficiency (%)* | Number of PIC per Nal |
|---|---|---|---|---|---|
| Nal | 126.5 ± 3.5 | 0.08 ± 0.01 | −19.6 ± 0.9 | N/A | N/A |
| PIC-Nal (6:1) | 142.5 ± 5.9 | 0.06 ± 0.01 | −13.6 ± 0.6 | 66.6 ± 2.3 | 39.9 ± 1.4 |
| PIC-Nal (4:1) | 139.8 ± 6.3 | 0.08 ± 0.01 | −13.4 ± 0.1 | 65.8 ± 4.3 | 39.9 ± 3.5 |
| PIC-Nal (2:1) | 141.5 ± 6.8 | 0.06 ± 0.02 | −13.7 ± 0.1 | 71.0 ± 2.7 | 42.6 ± 2.6 |

*Conjugation Efficiency (%): The molar ratio of PIC conjugated onto Nal to that added initially.

Figure 4:
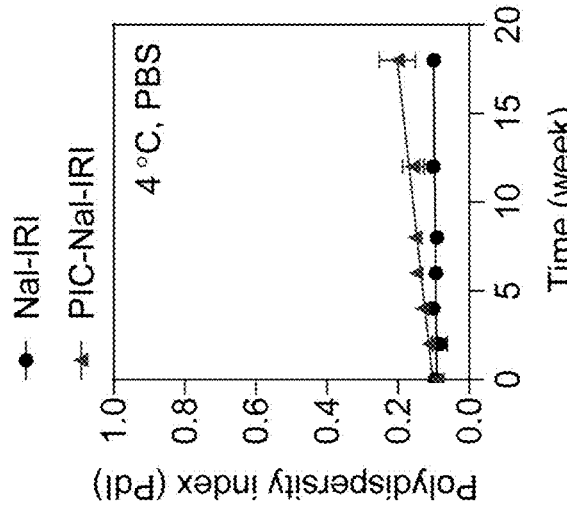
FIG. 4. Drug Release and the Stability of Nal-IRI and PIC-Nal-IRI. (a) Both Nal-IRI and PIC-Nal-IRI exhibited similar irinotecan release profiles in serum-containing medium at 37° C. The long-term stability of Nal-IRI and PIC-Nal-IRI (4° C., PBS) in dark was assessed by longitudinal monitoring of changes in (b) hydrodynamic size and (c) polydispersity index.
Figure 4:
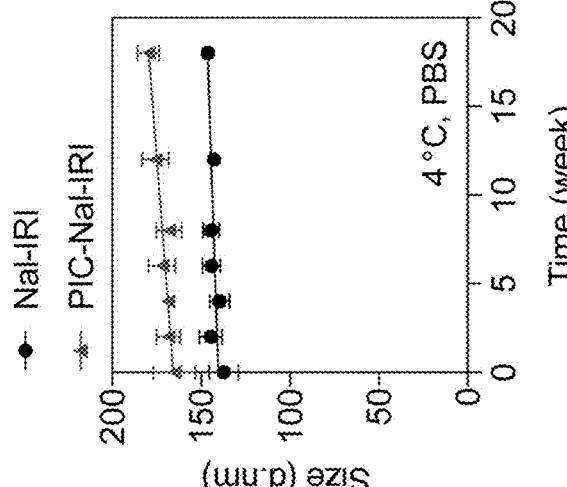
Figure 4:
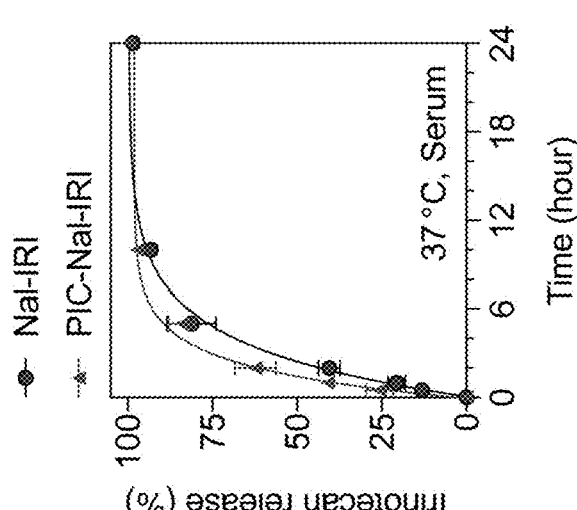

Irinotecan was passively encapsulated in the aqueous core of Nal and PIC-Nal at encapsulation efficiencies of 38.8±4.4% and 23.7±2.2%, respectively. The conjugation efficiency of PIC-Nal was 66.5±2.3%, which corresponded to 39.9±1.4 PICs per PIC-Nal. The conjugation efficiency of PIC to Nal-IRI was 48.0±2.7%, which corresponded to ~33 PICs per Nal-IRI. Drug release profiles of Nal-IRI and PIC-Nal-IRI were examined in human serum-containing medium (1% human serum) at 37° C. (FIG. 4a). At 1 hour post-incubation, we observed ~20% and ~42% release of irinotecan from the Nal-IRI and PIC-Nal-IRI, respectively. The relatively fast irinotecan release from PIC-Nal-IRI ($t_{1/2}$=2.3 h) compared to Nal-IRI ($t_{1/2}$=2 h) is likely due to the presence of PIC, suggesting that irinotecan will be readily available to the cancers cells when PIT occurs. Stability study suggested that 4-month dark storage at 4° C. did not significantly alter the overall size and monodispersity of Nal-IRI and PIC-Nal-IRI (FIG. 4b,c).

Photoactivity of PIC-Nal and PIC-Nal-IRI

Hydrophobic BPD molecules have a poor water solubility (<0.05 mg/mL) and readily aggregate in biologically relevant media, which hinders their photosensitizing efficacy (Chen B et al., *Liposomal delivery of photosensitising agents.* Expert Opin Drug Deliv, 2005, 2:477-487). Conjugation of BPD to pegylated Cet enhances BPD solubility and allows precise control of BPD quenching and de-quenching (Inglut C T et al., *Systematic Evaluation of Light-Activatable Biohybrids for Anti-Glioma Photodynamic Therapy.* J Clin Med 2019, 8(9):1269). It has previously been shown that self-quenched BPD molecules on Cet can be de-quenched by cancer cells upon lysosomal proteolysis of the Cet, and thereby increasing the tumor specificity (Inglut C T et al.,

*Systematic Evaluation of Light-Activatable Biohybrids for Anti-Glioma Photodynamic Therapy.* J Clin Med 2019, 8(9):1269; Huang H C et al., *Immobilization of Photo-Immunoconjugates on Nanoparticles Leads to Enhanced Light-Activated Biological Effects.* Small 2018:e1800236; Spring B Q et al., *Selective treatment and monitoring of disseminated cancer micrometastases in vivo using dual-function, activatable immunoconjugates.* Proc Natl Acad Sci USA 2014, 111(10):E933-E942). Prior to photoactivity evaluation, we confirmed that PIC, PIC-Nal and PIC-Nal-IRI do not alter the Q band of BPD (690 nm; FIG. 3a,b).

Due to the aggregation of BPD molecules in PBS, the absorbance values at 690 nm for free BPD and PIC in PBS were significantly reduced by ~64% and ~48%, respectively, compared to those fully dissolved in DMSO (FIG. 3c). On the other hand, PIC-Nal showed a less pronounced (~28%) loss of absorbance value at 690 nm in PBS compared to that fully dissolved in DMSO (FIG. 3c). This is believed to be due to the presence of PEG (~5 mol %) on the Nal that helps mitigate PIC aggregation in PBS. Loading of irinotecan into the aqueous core of PIC-Nal did not alter BPD's absorbance value at 690 nm (FIG. 3c).

Free BPD fluorescence is quenched in PBS due to aggregation of the hydrophobic BPD molecules (FIG. 3f). Both free BPD and PIC showed poor photoactivity due to the static fluorescence quenching of BPD molecules (FIG. 3d) (Savellano M D, Hasan T, *Targeting cells that overexpress the epidermal growth factor receptor with polyethylene glycolated BPD verteporfin photosensitizer immunoconjugates.* Photochem Photobiol 2003, 77:431-439; Inglut C T et al., *Systematic Evaluation of Light-Activatable Biohybrids for Anti-Glioma Photodynamic Therapy.* J Clin Med 2019, 8(9):1269; Huang H C et al., *Immobilization of Photo-Immunoconjugates on Nanoparticles Leads to Enhanced Light-Activated Biological Effects.* Small 2018:e1800236; Spring B Q et al., *Selective treatment and monitoring of disseminated cancer micrometastases in vivo using dual-function, activatable immunoconjugates.* Proc Natl Acad Sci USA 2014, 111(10):E933-E942). In contrast, fluorescence emission spectra of PIC-Nal and PIC-Nal-IRI were higher compared to that of free BPD and PIC. Furthermore, PIC-Nal and PIC-Nal-IRI exhibited up to 45% of photoactivity. This suggests that BPD molecules on PIC-Nal and PIC-Nal-IRI are more readily activated by light for PIT in biologically relevant media compared to PIC (FIG. 3d).

Highly reactive singlet oxygen ($^1O_2$) are generated by BPD after light excitation. The photoactivity (generation of $^1O_2$ yield after light activation) of free BPD, PIC, and PIC-Nal was next examined using singlet oxygen sensor green (SOSG) probes. Upon light activation at 690 nm, the SOSG fluorescence intensity generated by PIC-Nal was significantly higher than that of free BPD, PIC and Nal (FIG. 3e), suggesting that PIC-Nal has a higher $^1O_2$ yield than BPD, PIC, or Nal. To further showed that simply mixing PIC with Nal (i.e., 'PIC+Nal') does not improve the $^1O_2$ yield of PIC, it was validated that the enhanced $^1O_2$ yield of PIC-NP relies on successful click chemistry coupling of PIC-Nal. Selectivity and Uptake of PIC-Nal in Cancer Cells In addition to $^1O_2$ generation, therapeutic efficacy also depends in part on tumor selectivity and uptake capability. As demonstrated, conventional PIC and PIC decorated nanoparticles are tumor selective and readily up-taken by EGFR overexpressing cells (Huang H C et al., *Immobilization of Photo-Immunoconjugates on Nanoparticles Leads to Enhanced Light-Activated Biological Effects,* Small 2018, e1800236; M. D. Savellano, T. Hasan, *Targeting cells that overexpress the epidermal growth factor receptor with poly-*

*ethylene glycolated BPD verteporfin photosensitizer immunoconjugates,* Photochem Photobiol 2003, 77:431-439; B. Q. Spring et al., *Selective treatment and monitoring of disseminated cancer micrometastases in vivo using dual-function,* activatable immunoconjugates, Proc Natl Aca Sci USA 2014, 111: E933-942).

Figure 5:
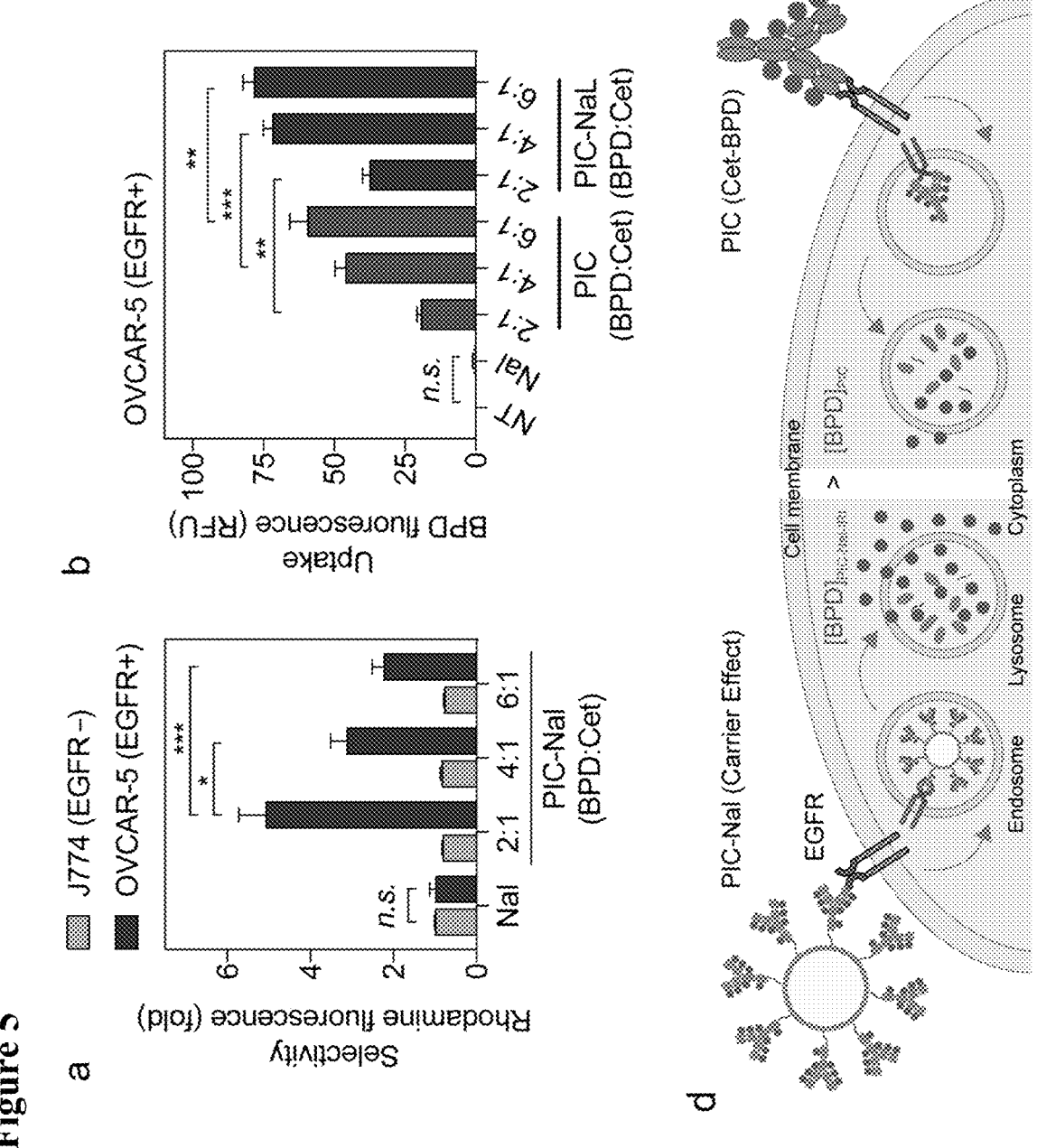
FIG. 5. Selective Binding, Uptake, and Imaging of PIC-Nal in Cancer Cells. (a) The selectivity of PIC-Nal was assessed in EGFR(−) J774 and EGFR(+) OVCAR-5 cells after 30 minutes of incubation. Nal alone was used as a control. The BPD:Cet ratio of PIC was varied (2:1, 4:1, 6:1). (b) The uptake of PIC-Nal and PIC in OVCAR-5 cells was assessed at 24 hours after incubation, based on intracellular BPD fluorescence signal. (c) Representative fluorescence images of OVCAR-5 incubated with BPD, PIC, or PIC-Nal for 24 hours. The BPD:Cet ratio of PIC was fixed at 6:1. Fluorescence signal of the nuclei (DAPI), BPD, and nano-liposome (rhodamine) shown in blue, green, and red, respectively (scale bar=35 μm). (d) Depiction of the 'carrier effect' of PIC-Nal in EGFR(+) cancer cells. (n>3; *P<0.05, ***P<0.001; n.s.: non-significant; one-way ANOVA, Tukey's posthoc test).
Figure 5:
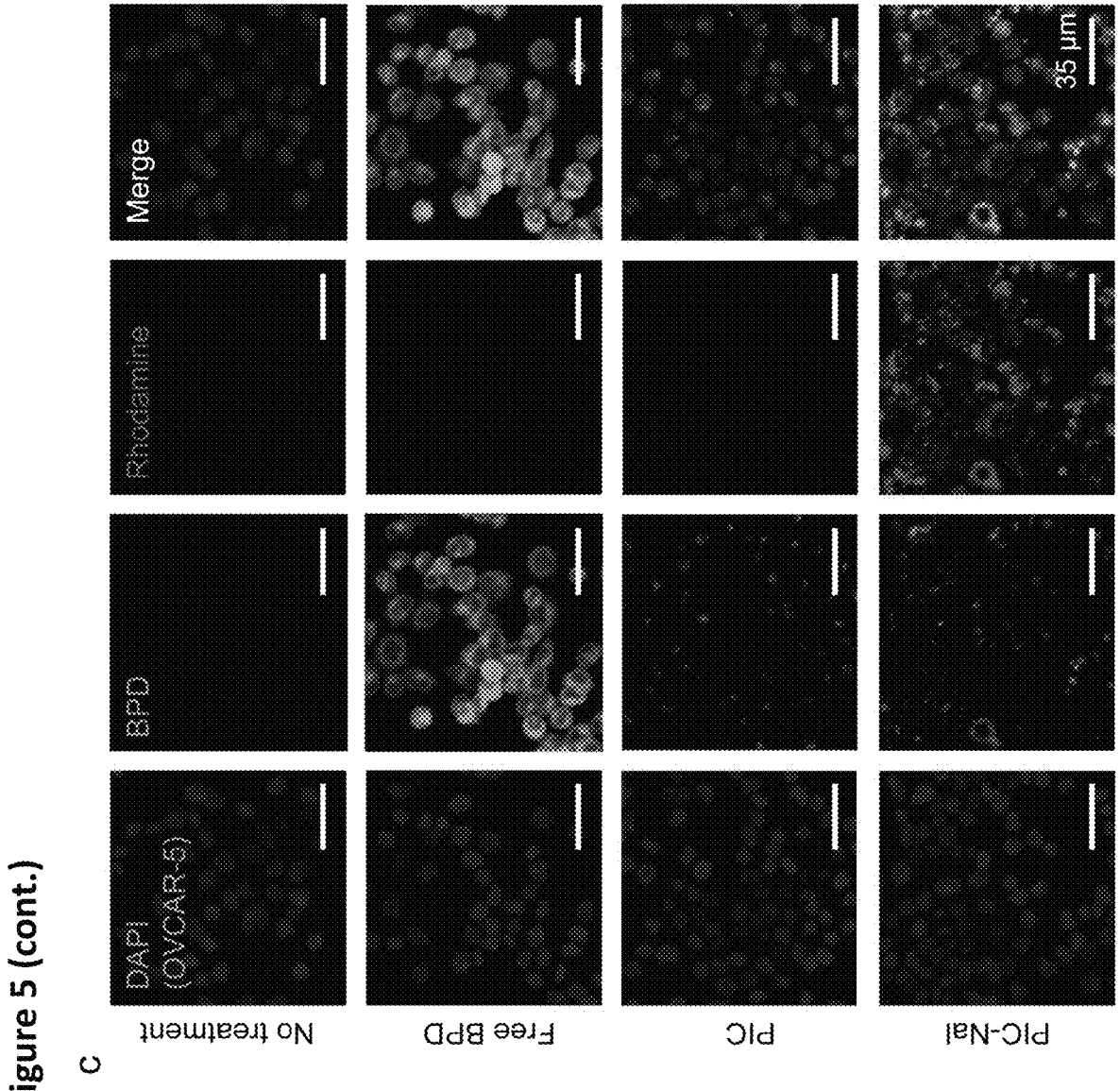

It was next investigated if PIC-Nal can selectively deliver Nal to EGFR-overexpressing cells by comparing the selective uptake of PIC-Nal and Nal in EGFR(+) OVCAR-5 ovarian cancer cells and EGFR(−) J774 macrophages at a fixed Nal concentration (0.5 µM based on rhodamine incorporation). After 30 minutes of incubation at 37° C., PIC-Nal uptake was 2-fold to 6-fold higher than Nal uptake in EGFR(+) OVCAR-5 cells (FIG. 5a). In contrast, PIC-Nal uptake was comparable to Nal uptake in EGFR(−) J774 macrophages. These results indicate PIC-Nal selectively binds to EGFR(+) cells, and are more likely to be internalized by EGFR+ cells, as compared to EGFR(−) cells. A reduction in EGFR-targeting capability of PIC-Nal was also observed with increasing BPD:Cet ratio from 2:1 to 6:1 (FIG. 5a), indicating excessive loading of BPD on Cet can compromise the selectivity of the antibody.

The persistent challenge of PIT has been insufficient delivery of photosensitizers by PIC. A phenomenon was observed in which conjugation of PIC on polymeric nanoparticles induces indirect endocytosis (carrying) of high payloads of PICs to targeted cells, which phenomenon is referred to herein as the 'carrier effect' (Huang H C et al., Immobilization of Photo-Immunoconjugates on Nanoparticles *Leads to Enhanced Light-Activated Biological Effects,* Small 2018, e1800236). Immobilization of PIC onto polymeric nanoparticles (poly(lactic-co-glycolic acid) (PLGA) nanoparticles) facilitated the indirect endocytosis of high payloads of PIC under limited antibody-receptor binding events, wherein the 'carrier effect' doubled the intra-tumoral PIC concentration in mice and resulted in a modest improvement in photoimmunotherapy response.

Figure 6:
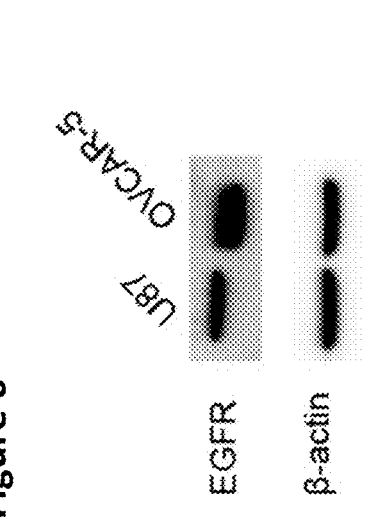
FIG. 6. Immunoblotting of EGFR in human OVCAR-5 and U87 cells. Whole cell extracts (40 μg) were loaded into each lane. β-actin was used as loading control. OVCAR-5 cell line has a higher EGFR expression compared to U87 cells.
Figure 7:
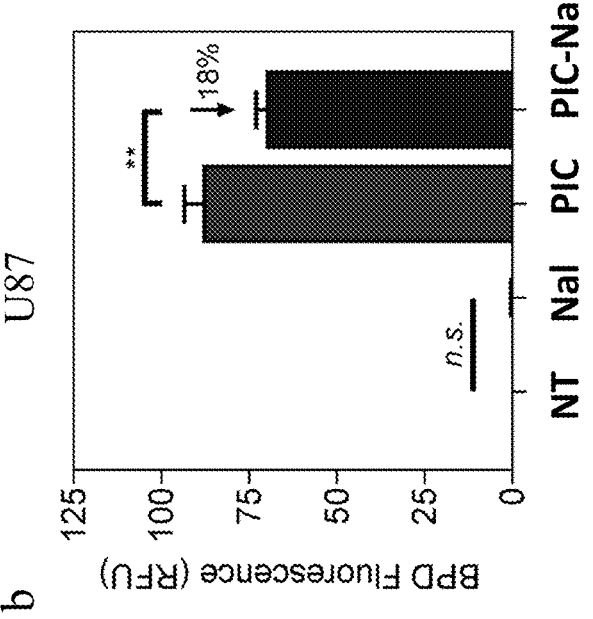
FIG. 7. Further analysis of Uptake of PIC and PIC-Nal in OVCAR-5 and U87 Cells. The uptake of PIC-Nal and PIC in OVCAR-5 cells (a) and U87 cells (b) was assessed at 24 hours after incubation, based on intracellular BPD fluorescence signal. PIC-Nal exhibited a modest increase of approximately 20% in intracellular BPD concentration compared to that of PIC in OVCAR-5 cells (a). In contrast, PIC-Nal exhibited a modest decrease of approximately 18% in intracellular BPD concentration compared to that of PIC in low EGFR-expressing U87 cells (b).
Figure 7:
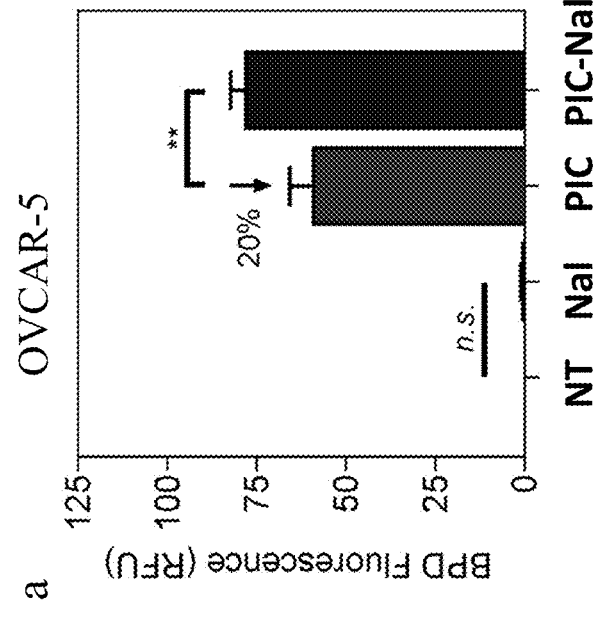

To validate if the 'carrier effect' is present for other nanocarriers, the intracellular delivery of BPD was compared between conventional PIC and PIC-Nal in two EGFR expressing cell lines: OVCAR-5 (high EGFR expressing) and U87 (low EGFR expressing) (FIG. 6). Intracellular BPD concentration was determined after the cells were incubated with either PIC (6:1; BPD per Cet) or PIC-Nal (6:1; BPD per Cet) at fixed 0.25 µM of BPD for 24 hours. Owing to the carrier effect, PIC-Nal exhibited a modest increase of approximately 20% in intracellular BPD concentration compared to that of PIC in OVCAR-5 cells (FIG. 7).

Figure 9:
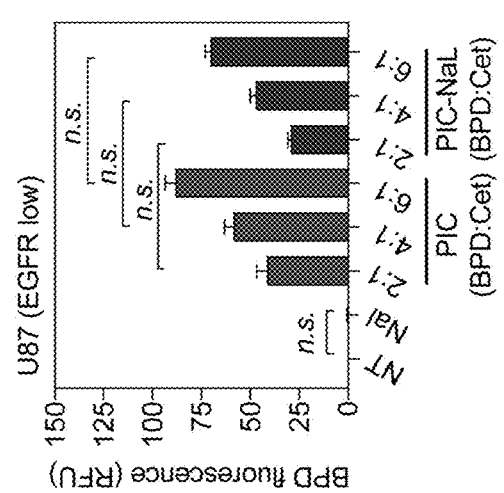
FIG. 9. Intracellular BPD fluorescence of PIC, and PIC-Nal at different BPD:Cet ratios (2:1, 4:1, 6:1) was evaluated in human glioma cells (U87) via extraction method. Cells were incubated with PIC or PIC-Nal at a fixed BPD concentration of 0.25 μM for 24 hours prior to extraction (n>3; n.s.: non-significant; one-way ANOVA, Tukey's posthoc test).

We next tested if cancer-selective PIC-Nal can improve the overall uptake of PIC in EGFR-overexpressing OVCAR-5 cells at 24 hours post-incubation. Compared to PIC alone, it was observed that PIC-Nal proportionally enhances (P<0.05) the intracellular BPD uptake by 95%, 56%, and 32% at BPD:Cet molar ratio of 2:1, 4:1, and 6:1, respectively (FIG. 5b). Owing to the 'carrier effect', PIC-Nal exhibited a modest increase of approximately 20% in intracellular BPD concentration compared to that of PIC in OVCAR-5 cells. In contrast, this 'carrier effect' was not present in the low EGFR expressing U87 cells when comparing intracellular BPD concentration of PIC and PIC-Nal (FIG. 9). Intracellular BPD concentration depends on the number of BPD molecules delivered to the cell. As expected, an increase in BPD fluorescence was observed for OVCAR-5 cells when comparing PIC and PIC-Nal at different BPD-to-Cet molar ratio (FIG. 5b).

Leveraging the diagnostic capabilities of BPD fluorescence, the intracellular uptake of free BPD, PIC, and PIC- Nal was visualized in OVCAR-5 cells at 24 hours post-incubation (FIG. 5c). Hydrophobic BPD can easily partition into the plasma membrane of both cancer and non-malignant cells. Thus, it is not surprising that free BPD shows the highest uptake in OVCAR-5 cells compared to PIC and PIC-Nal. However, free BPD lacks selectivity against EGFR-overexpressing cancer cells, and thus will more likely induce off-target phototoxicity in vivo. Fluorescence microscopy images showed that PIC-Nal modestly enhanced intracellular BPD accumulation compared to PIC alone (FIG. 5c), which agrees with findings using the extraction method (FIG. 5b). Incubation with PIC-Nal led to a significant intracellular accumulation of Nal, indicated by the intense rhodamine fluorescence signals (FIG. 5c). This suggests the capability of delivering another therapeutic agent at a high payload using PIC-Nal. These studies verified that PIC-Nal not only enables EGFR-targeted delivery of Nal but also serves as an efficient platform to enhance PIC uptake in EGFR(+) cancer cells (FIG. 5d).

PIC-Nal Delivers Irinotecan for Synergistic Photoimmuno-Chemotherapy In Vitro

PDT therapeutic efficacy relies in part on intracellular accumulation of photosensitizers. Covalent conjugation of PICs onto nanoliposomes improved BPD uptake in OVCAR-5 cells. However, PIC-mediated intracellular BPD accumulation is higher than that of PIC-Nal in U87 cells.

Figure 8:
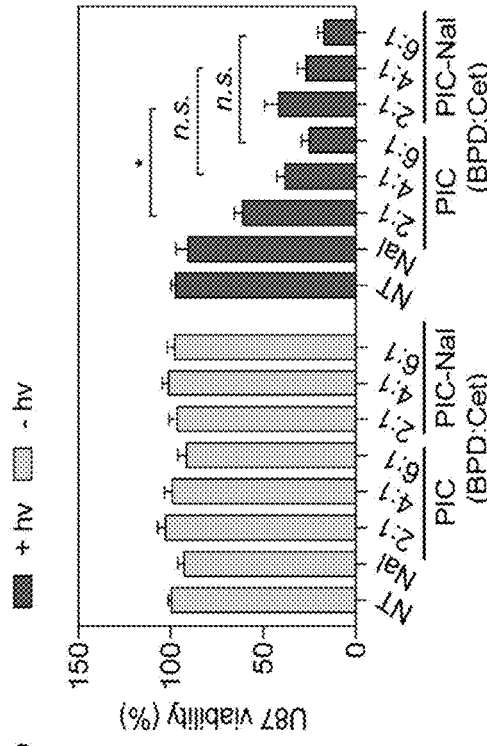
FIG. 8. Phototoxicity of photo-immunoconjugate nanoliposome (PIC-Nal) at different BPD:Cet ratios in (a) human ovarian cancer cells (OVCAR-5) and (b) human glioma cancer cells (U87). Cells were incubated with PIC or PIC-Nal at a fixed BPD concentration of 0.25 μM for 24 hours before light activation at 690 nm (20 J/cm2, 150 mW/cm2, bottom illumination). Cell viability was determined by MTT assay at 24 hours after PIT. (n>3; *P<0.05; one-way ANOVA, Tukey's posthoc test).
Figure 8:
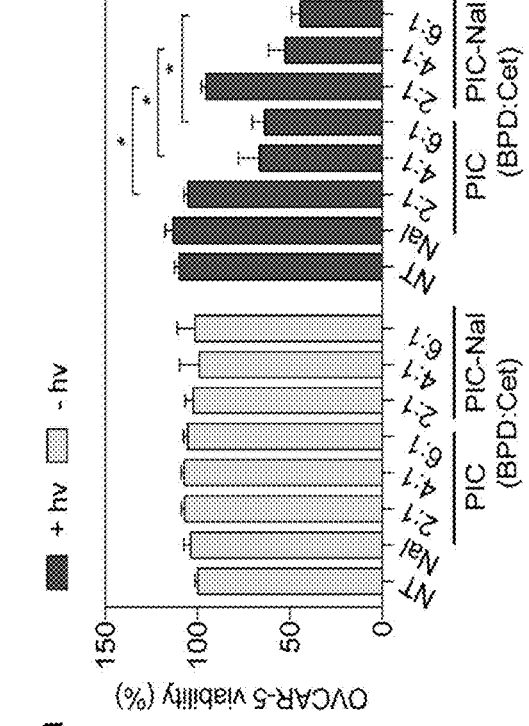
Figure 10:
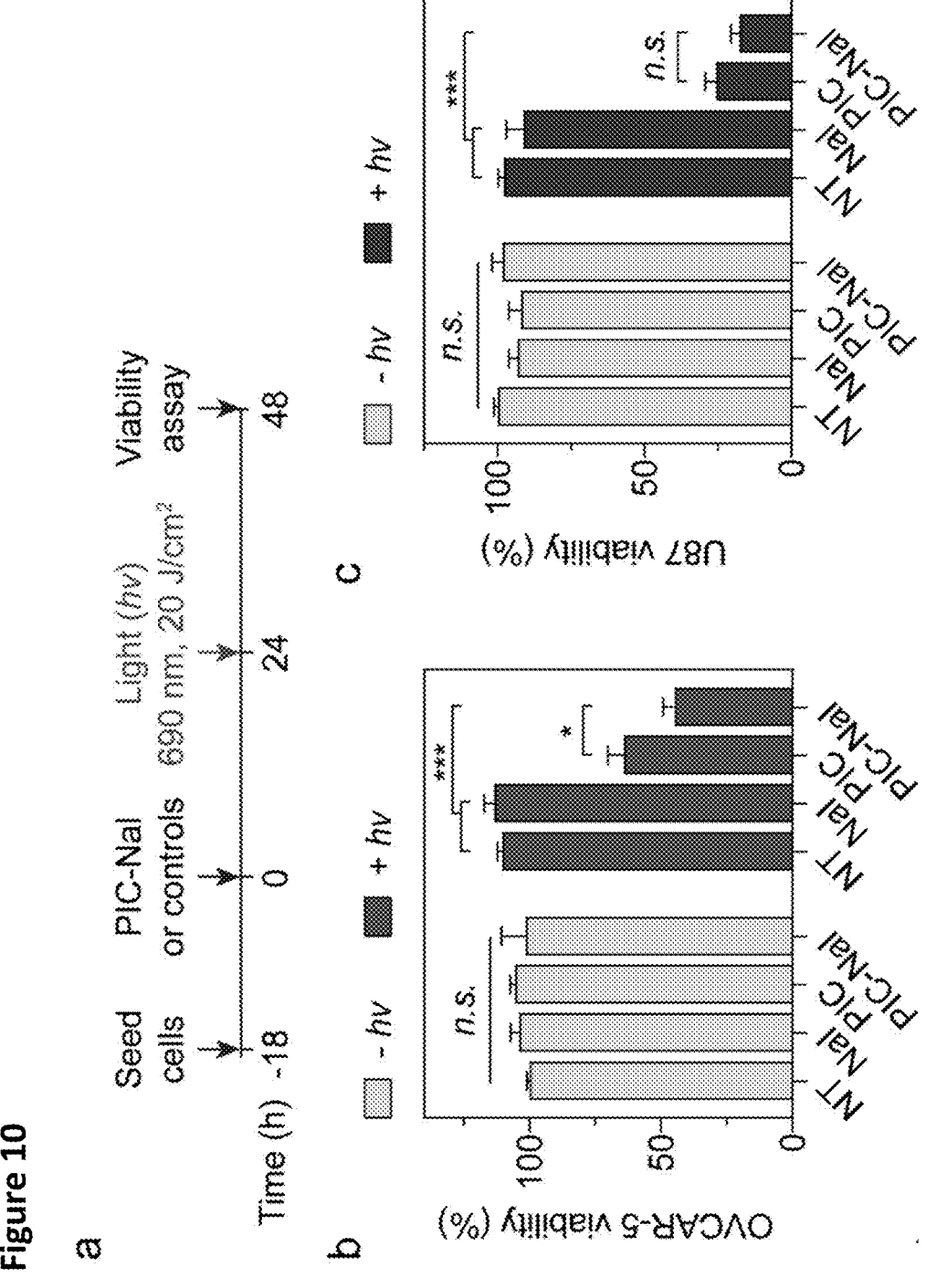
FIG. 10. Phototoxicity of PIC-Nal and PIC in OVCAR-5 and U87 cells. (a) Cells were incubated with PIC or PIC-Nal at a fixed BPD concentration (0.25 μM) for 24 hours prior to light activation (690 nm, 20 J/cm2, 150 mW/cm2). Cell viability was determined by MTT assay at 24 hours post-light activation. PIC-Nal is more phototoxic than PIC in (b) high EGFR-expressing OVCAR-5 but not in (c) low EGFR-expressing U87. (d,e) While increase in BPD uptake in OVCAR-5 cells for the PIC-Nal treatment resulted in enhanced phototoxicity, there was no significant difference in U87 cell killing between PIC and PIC-Nal treatment, despite PIC incubation resulted in higher intracellular BPD accumulation. (n>3; *P<0.05, ***P<0.001; n.s.: non-significant; one-way ANOVA, Tukey's posthoc test). The findings of the two graph correlates intracellular BPD content (fluorescence with cell viability).
Figure 10:
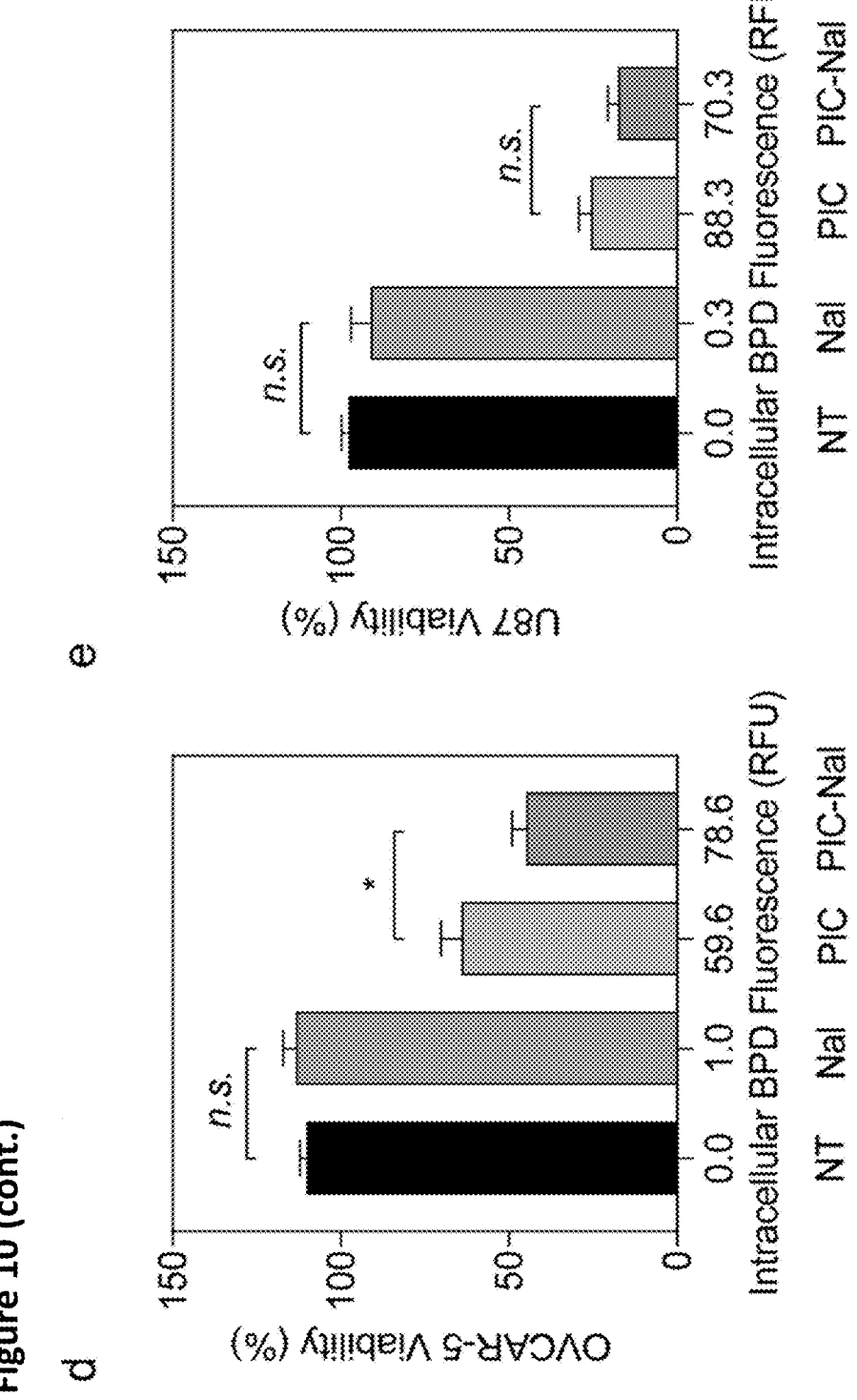

It was investigated if PIC-Nal is more phototoxic than PIC using OVCAR-5 cells. U87 cells expressing lower EGFR levels served as a control (FIG. 6). At 24 hours of incubation at a fixed BPD concentration of 0.25 μM, Nal, PIC and PIC-Nal show negligible dark toxicity in either OVACAR-5 or U87 cell line (FIG. 10b, c). However, with light irradiation at 20 J/cm$^2$ after incubation, PIC-Nal significantly reduced OVCAR-5 viability by about 60%, compared to about 35% viability reduction achieved by using PIC at a fixed BPD:Cet ratio of 6:1 (FIG. 10b). However, there was no significant difference in cell viability between the PIC-Nal and PIC treatment in U87 cells (FIG. 10c). This is believed to be due to the lower EGFR expression in U87 cells compared to that of OVCAR-5 cells, indicating that the 'carrier effect' is in part EGFR dependent and the lack of significant difference in BPD uptake between PIC and PIC-Nal (FIG. 9) Similar results were observed in OVCAR-5 cells using PIC and PIC-Nal with lower BPD:Cet ratio of 2:1 and 4:1 (FIG. 8a), wherein PIC-nanoliposome conjugation induced more effective cell killing. However, a significant difference in cell viability was only observed when using PIC with low BPD:cetuximab ratio (2:1) in U87 cells (FIG. 8b).

Figure 11:
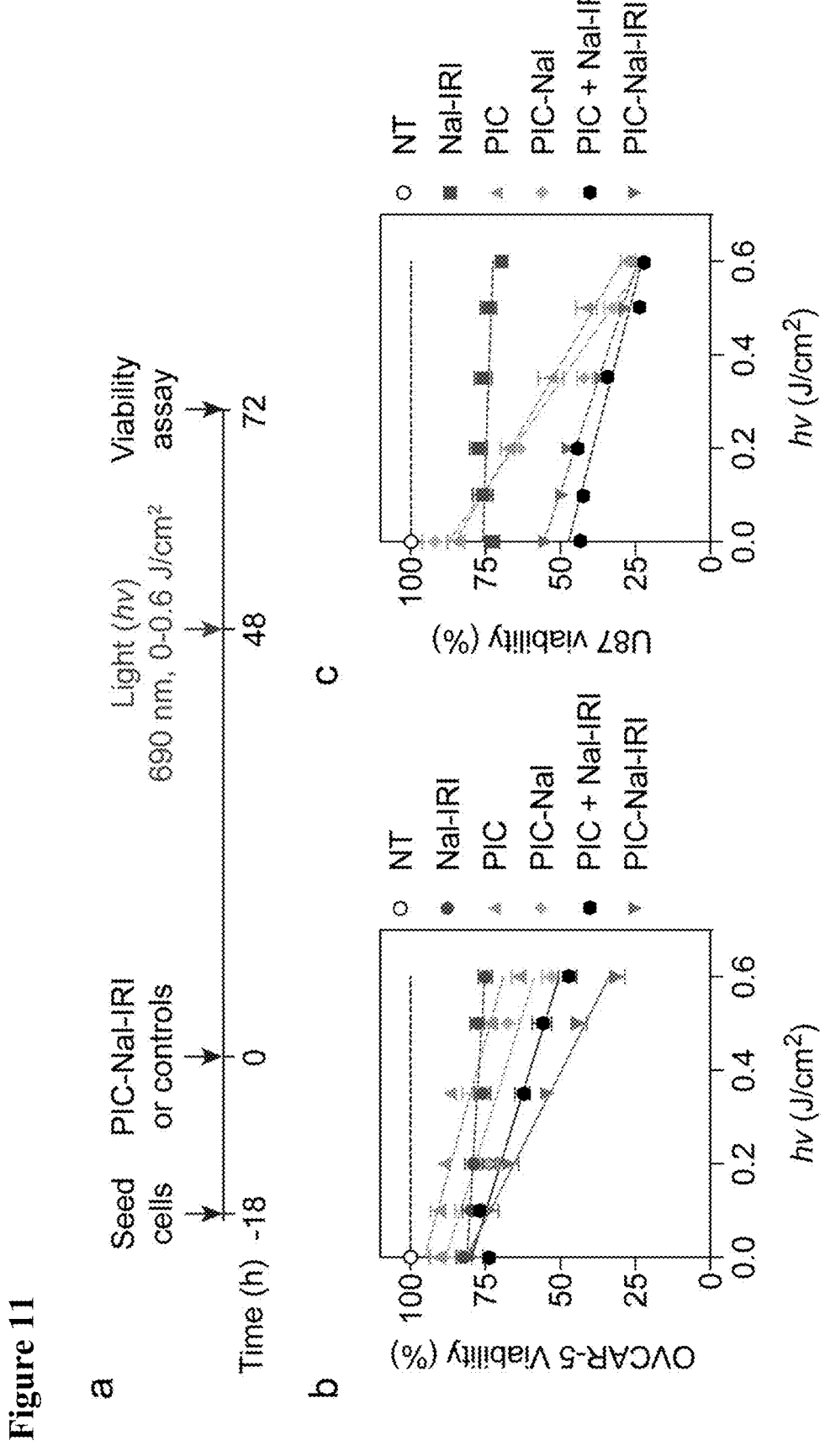
FIG. 11. Combination of PIT and Nal-IRI in OVCAR-5 and U87 cells. (a) Cells were incubated with PIC-Nal-IRI or controls at a fixed BPD (1 μM) and irinotecan (7 μM) concentration for 48 hours prior to light activation (690 nm, 10 mW/cm², 0-0.6 J/cm²). (b) OVCAR-5 viability and (c) U87 viability were determined by MTT assay at 24 hours post-light activation. The $IC_{50}$ values of PIC-Nal are ~0.6 μMxJ/cm² and ~0.35 MxJ/cm² for (d) OVCAR-5 and (e) U87 cells, respectively. (d, e) The reduction of cell viability was compared among the treatment groups. (f, g) Combination index (CI) was determined using CompuSyn software. The CI value quantitatively defines synergism (CI<1), additive effect (CI=1) and antagonism (CI>1) effect of light-activated PIC-Nal-IRI in OVCAR-5 and U87 cells. (n>3; *P<0.05, ***P<0.001; n.s.: non-significant; one-way ANOVA, Tukey's posthoc test).
Figure 11:
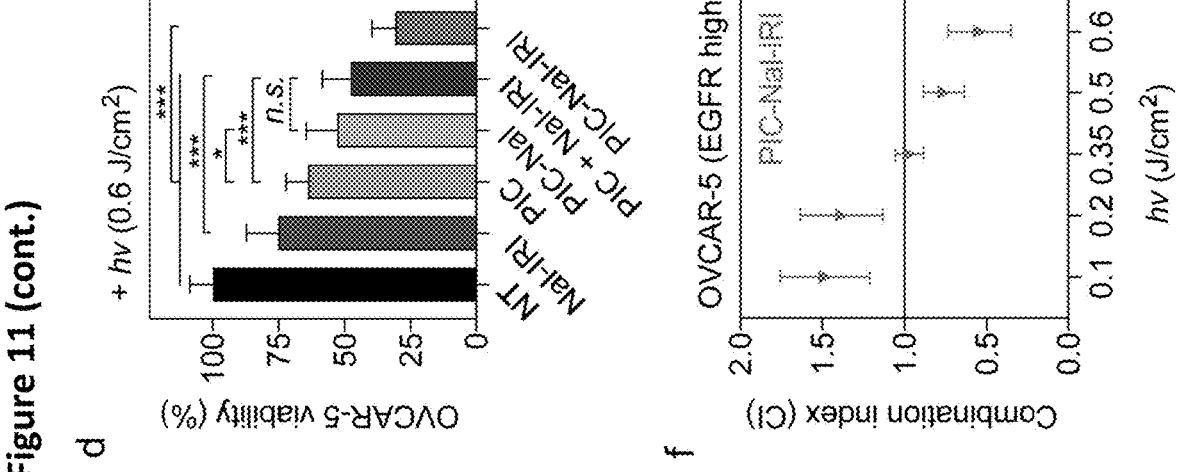

PIC-Nal not only improves PIT efficacy against EGFR-overexpressing cancer cells, but also provides a mechanism to simultaneously co-deliver irinotecan chemotherapy, thereby further enhancing treatment outcomes. The therapeutic efficacy of PIC-Nal-IRI was next evaluated at various light fluences (0-0.6 J/cm$^2$) in OVCAR-5 and U87 cells (FIG. 11a). Control groups included Nal-IRI alone, PIC alone, PIC-Nal alone, and simply mixing PIC with Nal-IRI ('PIC+Nal-IRI') at fixed drug concentrations (i.e., irinotecan: 7 μM and BPD: 1 μM). The molar ratio of BPD-to-Cet was fixed at 6:1. In OVCAR-5 (FIG. 11b) and U87 cells (FIG. 11c), 72 hours of Nal-IRI-treatment reduced cell viability by ~20-25%. Light activation of Nal-IRI alone did not alter the cell viability (P>0.05). Both PIC and PIC-Nal alone showed minimal dark toxicity (<15% viability reduction) (FIG. 11b,c). A light dose dependent reduction in cell viability was observed in both PIC- and PIC-Nal-treated cells. PIC-Nal was consistently found to be ~10-15% more phototoxic compared to PIC alone in OVCAR-5, but not in U87 cells. The IC$_{50}$ of PIC-Nal upon light activation was approximately 0.6 μM×J/cm$^2$ and 0.35 μM×J/cm$^2$ for OVCAR-5 and U87 cells, respectively (FIG. 11b,c). In OVCAR-5 cells, while both PIC-Nal-IRI and 'PIC+Nal-IRI' showed similar phototoxicity at 0.2 J/cm$^2$ or below, it was observed that PIC-Nal-IRI out-performs 'PIC+Nal-IRI' at or above 0.35 J/cm$^2$ (FIG. 11b). At 0.6 μM×J/cm$^2$, PIC-Nal-IRI was ~20% more cytotoxic than 'PIC+Nal-IRI' in OVCAR-5 cells (P<0.001) (FIG. 11d). In contrast, both PIC-Nal-IRI and 'PIC+Nal-IRI' showed similar phototoxicity in U87 cells (FIG. 11e).

The combination interactions between the no-treatment (NT), PIC alone, Nal-IRI alone, and PIC-Nal-IRI groups were further evaluated (FIG. 11f,g). Using CompuSyn software and robust regression fits of the dose-response curve trend lines (R$^2$=0.914-0.999) (Chou T C, Theoretical basis, experimental design, and computerized simulation of synergism and antagonism in drug combination studies. Pharmacol Rev 2006, 58:621-681; Chou T C, Talalay P, Quantitative analysis of dose-effect relationships: the combined effects of multiple drugs or enzyme inhibitors. Adv Enzyme Regul 1984, 22:27-55), the combination index (CI) values were calculated to determine if combination of PIT and Nal-IRI using PIC-Nal-IRI is synergistic (CI<1), additive (CI=1), or antagonistic (CI>1). In OVCAR-5 cells, the combination of PIT and Nal-IRI using PIC-Nal-IRI was additive at 0.3 J/cm$^2$ (CI=0.97±0.09), and synergistic at 0.5 and 0.6 J/cm$^2$ (CI=0.76±0.12 and 0.54±0.19, respectively). Therapeutic synergy was observed in a light dose dependent manner in OVCAR-5 cells (FIG. 11f) but not in U87 cells (CI=1.2±0.1) (FIG. 11g).

Multi-Tier Cellular Targeting Using PIC-Nal-IRI

Figure 12:
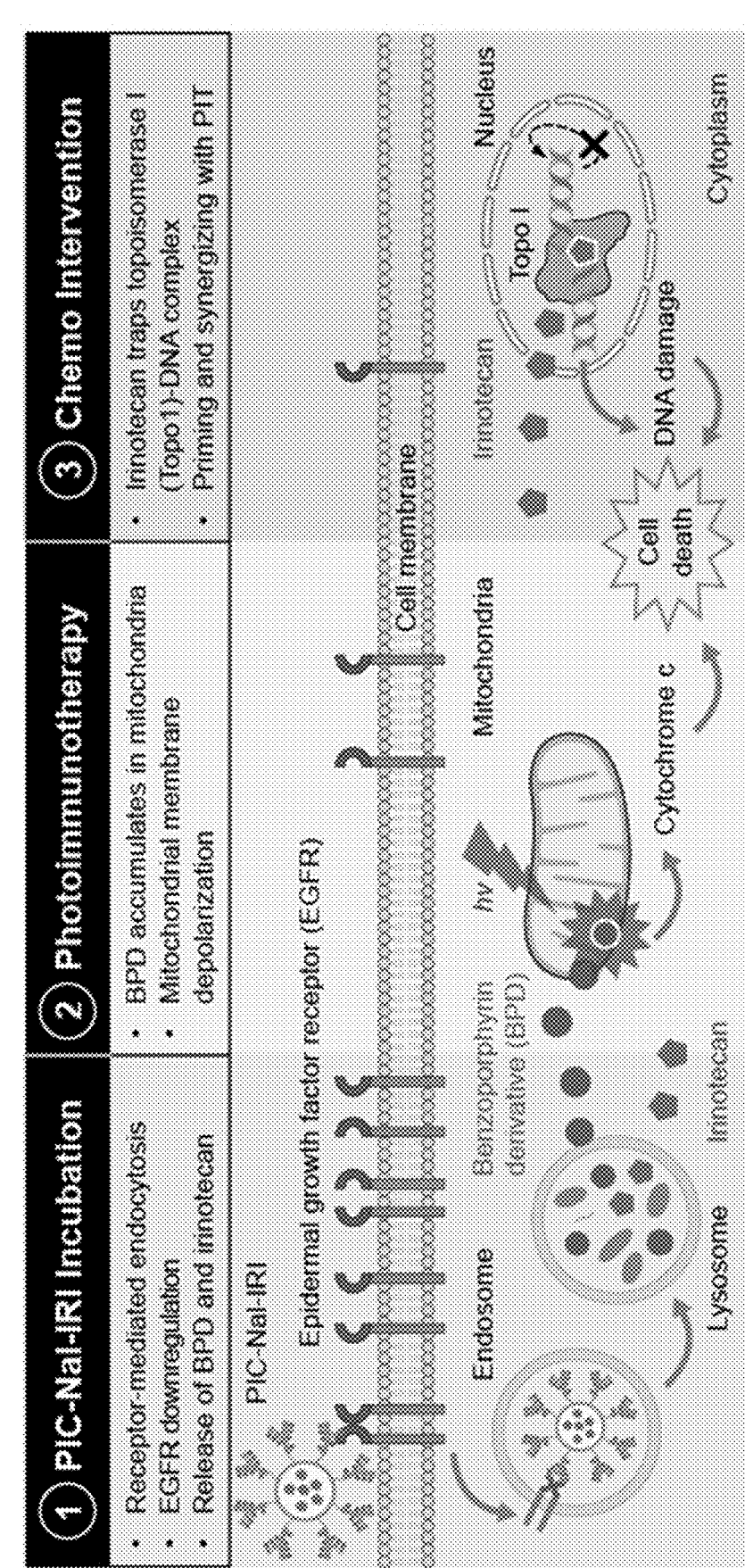
FIG. 12. Multi-Tier Cancer Targeting. (a) Schematic of multi-tier cancer targeting mechanism: (1) EGFR binding, endocytosis, and proteolysis of PIC-Nal-IRI, (2) PIT-mediated depolarization of mitochondrial membrane potential, and (3) irinotecan-induced DNA damage, leading to synergistic cell killing. (b) Immunoblotting of EGFR and γ-H2AX expression in OVCAR-5 cells at different time points after treatment. Quantitative analyses of normalized (c) EGFR and (d) γ-H2AX expressions in OVCAR-5 cells. (e) Mitochondrial membrane depolarization was assessed at 24 hours post-light irradiation (0.35 J/cm², 10 mW/cm²). (n=3; *P<0.05; P<0.01; *P<0.001; n.s.: non-significant; one-way ANOVA, Tukey's posthoc test).
Figure 12:
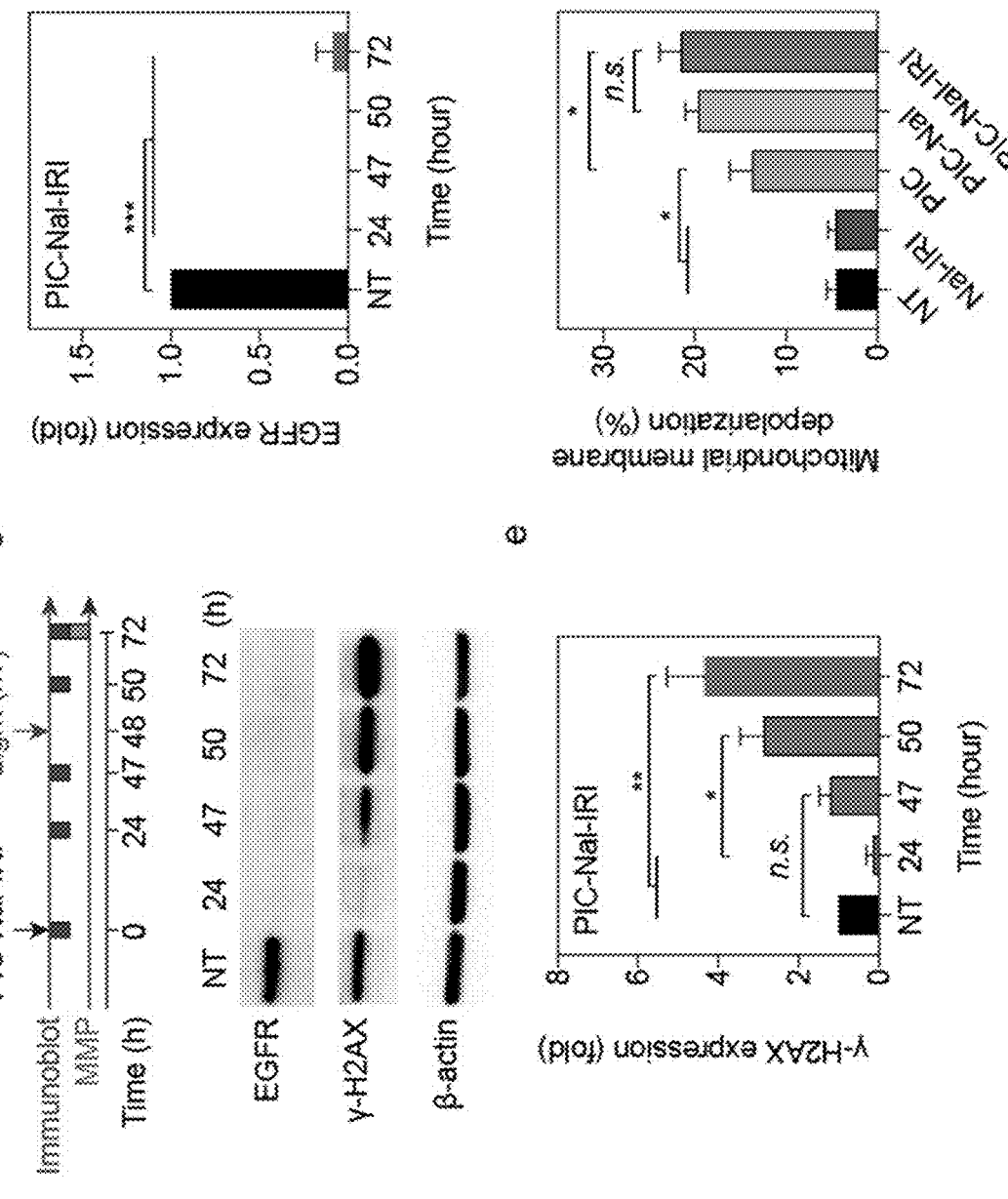
Figure 13:
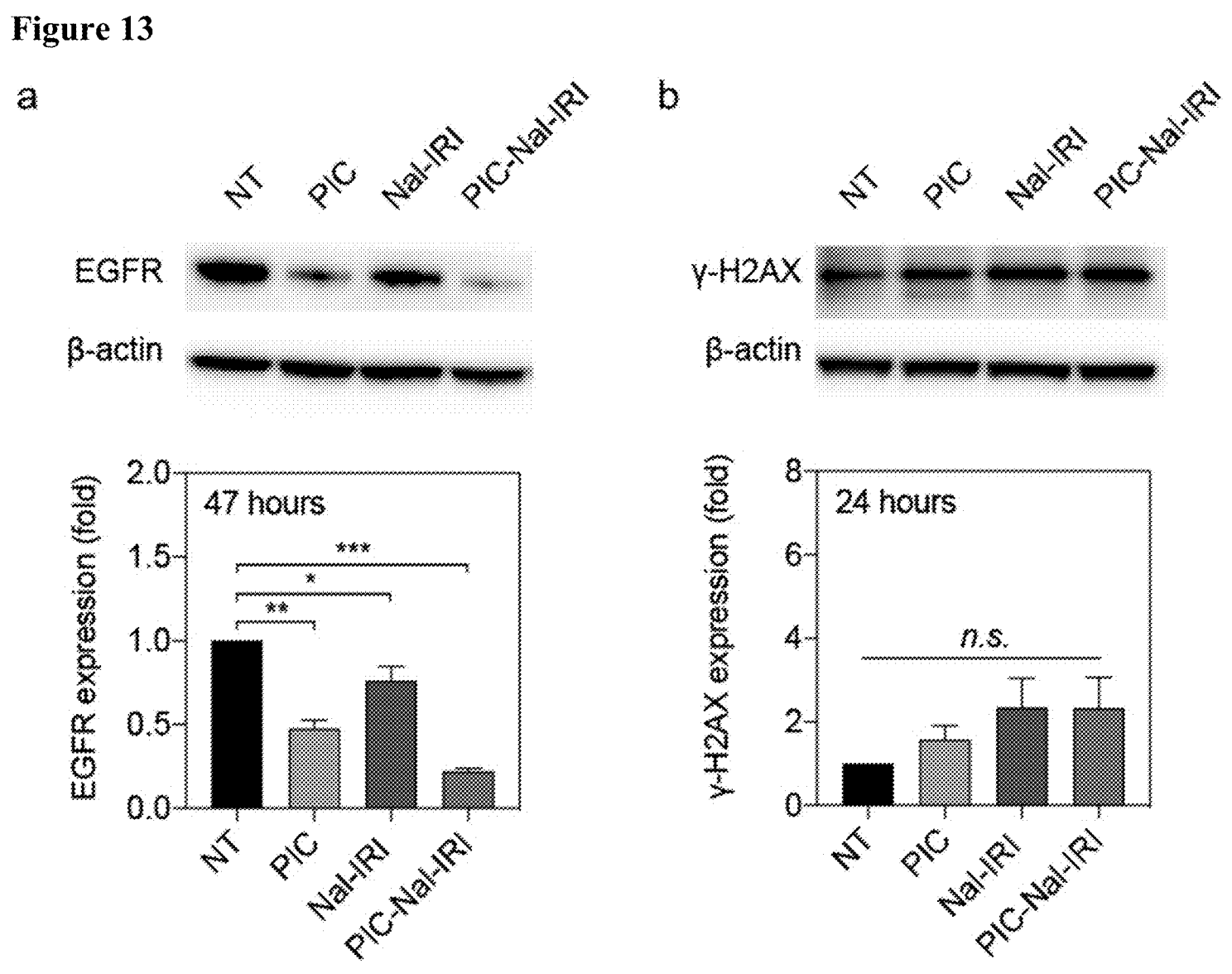

The uniqueness of PIC-Nal-IRI lies, in part, in the multi-tier cellular targeting abilities. Three mechanistically distinct therapeutics (i.e., Cet, BPD, and irinotecan) were incorporated in PIC-Nal-IRI to target the EGFR, mitochondria, and DNA, respectively (FIG. 12a). Downregulation of total EGFR expression was observed after 24 hours of PIC-Nal-IRI incubation and persisted throughout the treatment duration up to 72 hours (FIG. 12b,c). Nal-IRI alone did not alter the EGFR expression (FIG. 13a). Irinotecan induced DNA damage was evaluated by monitoring the expression level of γ-H2AX (Kuo L J, Yang L X, Gamma-H2AX—a novel biomarker for DNA double-strand breaks. In Vivo 2008, 22:305-309). PIC-Nal-IRI significantly upregulated γ-H2AX expression at 72 hours post-incubation (FIG. 12d), indicating DNA double-strand breaks. γ-H2AX expression was similar across all different groups (i.e., NT, Nal-IRI, PIC, and PIC-Nal-IRI) at 48 hours post-incubation (FIG. 13b). Proteolyzed PIC co-localizes to mitochondria after 24 hours and induces mitochondrial membrane potential (ΔΨm) depolarization upon light activation in glioma cells (Inglut C T et al., Systematic Evaluation of Light-Activatable Biohybrids for Anti-Glioma Photodynamic Therapy. J Clin Med 2019, 8(9):1269). ΔΨm depolarization was measured in OVCAR-5 cells at 24 hours after light activation PIC-Nal-IRI or controls (FIG. 12e). Light activation of PIC, PIC-Nal, or PIC-Nal-IRI all induced a high level of ΔΨm depolarization in OVCAR-5 cells (FIG. 12e). No ΔΨm depolarization was observed using Nal-IRI alone (FIG. 12e).

Further Discussion

Therapeutic treatment utilizing a combination of two or more therapeutic modalities has been demonstrated to be most effective against many cancer malignancies due to the additive or synergistic effects of the two drugs. PIC is a promising and exciting tool in the armamentarium for cancer treatment, surgery, and imaging (van Dongen G A et al., *Photosensitizer-antibody conjugates for detection and therapy of cancer*. Adv Drug Deliv Rev 2004, 56:31-52; Mitsunaga M et al., *Cancer cell-selective in vivo near infrared photoimmunotherapy targeting specific membrane molecules*. Nat Med 2011, 17:1685-1691; Schmidt S et al., *Clinical use of photodynamic therapy in gynecologic tumor patients—antibody-targeted photodynamic laser therapy as a new oncologic treatment procedure*. Zentralbl Gynakol 1992, 114:307-311; Spring B Q et al., *Selective treatment and monitoring of disseminated cancer micrometastases in vivo using dual-function, activatable immunoconjugates*. Proc Natl Acad Sci USA 2014, 111(10):E933-E942). However, the selectivity-uptake trade-off has heretofore been a major challenge, limiting the prior applications of PIC technology.

Previous works have shown that PIC (Cet-BPD) is highly selective against cancer cells overexpressing EGFR with 20-fold less accumulation in low EGFR cells (Savellano M D, Hasan T, *Targeting cells that overexpress the epidermal growth factor receptor with polyethylene glycolated BPD verteporfin photosensitizer immunoconjugates*. Photochem Photobiol 2003, 77:431-439; Abu-Yousif A O et al., *Epidermal growth factor receptor-targeted photosensitizer selectively inhibits EGFR signaling and induces targeted phototoxicity in ovarian cancer cells*. Cancer Lett 2012, 321:120-127; Savellano M D, Hasan T, *Photochemical targeting of epidermal growth factor receptor: a mechanistic study*. Clin Cancer Res 2005, 11:1658-1668). The Cet-BPD also has a high tumor-to-normal tissue ratio (T/N) of 9.2, which mitigates bowel phototoxicity (Spring B Q et al., *Selective treatment and monitoring of disseminated cancer micrometastases in vivo using dual-function, activatable immunoconjugates*. Proc Natl Acad Sci USA 2014, 111(10):E933-E942). Despite high tumor selectivity, it was discovered that the intracellular uptake of Cet-BPD is 6-fold less than that of free BPD in EGFR-overexpressing cancer cells, significantly reducing the anti-cancer phototoxicity by 20-fold (Inglut C T et al., *Systematic Evaluation of Light-Activatable Biohybrids for Anti-Glioma Photodynamic Therapy*. J Clin Med 2019, 8(9):1269). To break through this selectivity-uptake trade-off, the present disclosure provides for an engineering approach that leverages click chemistry to covalently tether large amounts of PICs (Cet-BPD) onto the surface of a NaI. As demonstrated herein, PIC-NaI is not only highly selective to EGFR-overexpressing OVCAR-5 cells with 2-fold to 5-fold less accumulation macrophage cells, but also enhances PIC uptake in OVCAR-5 by ~20-30%. The disclosed constructs and methodologies thus overcome the selectivity-uptake challenges and substantially improve the overall photoimmunotherapeutic efficacy.

Similar results were observed using PIC-poly(lactic-co-glycolic acid) nanoparticles (PIC-NP) in OVCAR-5 and U87 cells, indicating the generalizability of the disclosed techniques (see, e.g., Huang H C et al., *Immobilization of Photo-Immunoconjugates on Nanoparticles Leads to Enhanced Light-Activated Biological Effects*. Small 2018: e1800236). However, unlike PIC-NP, in this study, PIC-NaI did not enhance the PIC accumulation in low EGFR-expressing U87 cells. It is believed that this discrepancy is attributed to the larger construct size (steric hindrance) and a lower PIC surface density of PIC-NaI (~150 nm, ~32 PICs per NaI) as compared to the smaller PIC-NP (~100 nm) with a higher PIC surface density (~75 PICs per NP). It has been reported that cytoplasmic rigidity could limit the internalization of larger particles with radii above the optimal radius (typically around 50 nm) via receptor-mediated endocytosis (Gonzalez-Rodriguez D, Barakat A I, *Dynamics of receptor-mediated nanoparticle internalization into endothelial cells*. PLOS One 2015, 10:e0122097). It has also been reported that increasing antibody coverage on the surface of nanoparticles or antibody-receptor binding affinity can improve receptor-mediated endocytosis (Vácha R et al., *Receptor-Mediated Endocytosis of Nanoparticles of Various Shapes*. Nano Letters 2011, 11:5391-5395). Based on the present data, it is believed that conjugation of PICs onto a nanoplatform to boost the cancer-selective PIC uptake is contingent in part upon several factors, including particle size, PIC density, and PIC binding affinity of the nanoplatforms.

PDT has been shown to reverse chemoresistance, synergize with chemotherapeutics and biologics, and overcome compensatory survival pathways used by cancer cells to evade treatment (Spring B Q et al., *The role of photodynamic therapy in overcoming cancer drug resistance*. Photochem Photobiol Sci 2015, 14:1476-1491; Baglo Y et al., *Porphyrin-lipid assemblies and nanovesicles overcome ABC transporter-mediated photodynamic therapy resistance in cancer cells*. Cancer Letters 2019, 457:110-118; Gallagher-Colombo S M et al., *Erlotinib Pretreatment Improves Photodynamic Therapy of Non-Small Cell Lung Carcinoma Xenografts via Multiple Mechanisms*. Cancer Res 2015, 75:3118-3126; Luo D et al., *Intrabilayer 64Cu Labeling of Photoactivatable, Doxorubicin-Loaded Stealth Liposomes*. ACS Nano 2017, 11:12482-12491; Rizvi I et al., *Synergistic Enhancement of Carboplatin Efficacy with Photodynamic Therapy in a Three-dimensional Model for Micrometastatic Ovarian Cancer*. Cancer Res 2010, 70(22):9319-28). It has also been shown that PDT synergizes with irinotecan to reduce metastatic burden and improve survival outcomes in pancreatic tumor mouse models via a two-way mechanism in which (i) PDT photodamages ABCG2 drug efflux transporters to prevent irinotecan efflux, and (ii) irinotecan alleviates PDT-induced tumor hypoxia (Huang H C et al., *Photodynamic Priming Mitigates Chemotherapeutic Selection Pressures and Improves Drug Delivery*. Cancer Res 2018, 78:558-571; Huang H C et al., *Photodynamic Therapy Synergizes with Irinotecan to Overcome Compensatory Mechanisms and Improve Treatment Outcomes in Pancreatic Cancer*. Cancer Res 2016, 76:1066-1077; Pigula M et al., *Size-dependent Tumor Response to Photodynamic Therapy and Irinotecan Monotherapies Revealed by Longitudinal Ultrasound Monitoring in an Orthotopic Pancreatic Cancer Model*. Photochem Photobiol 2019, 95(1):378-386). However, prior studies utilized non-targeted nanoliposomal irinotecan and unquenched photosensitizers that are at a higher risk of normal tissue toxicity. In accordance with the present disclosure, irinotecan is reproducibly incorporated into PIC-NaI constructs for synergistic, targeted photoimmuno-chemotherapy.

It has been shown that the therapeutic synergy of combination treatments depends, in part, on the delivery of fixed drug molar ratio to the cancer cells (Tolcher A W, Mayer L D, *Improving combination cancer therapy: the CombiPlex® development platform*. Future Oncol 2018, 14:1317-1332). The disclosed PIC-NaI-IRI constructs, co-delivering a fixed irinotecan-to-BPD molar ratio at 7:1, may be activated by light at low light fluences (0.5-0.6 J/cm$^2$) for synergistic reduction of cancer cell viability (CI<0.76). Moreover, the particular irinotecan-to-PIC ratio in PIC-NaI-IRI may be altered depending on the particular application.

As demonstrated herein, PIC-NaI-IRI exhibits significantly higher OVCAR-5 cell phototoxicity by 20% (P<0.001), as compared to the unconjugated mixtures of 'PIC+Nal-IRI,' which is an often-overlooked control during the development of multi-drug nanomedicine. In low EGFR expressing U87 cell, PIC-Nal-IRI and unconjugated mixtures of 'PIC+Nal-IRI' had similar phototoxicity at 0.35 J/cm$^2$ (viability: 34.9±2.0% vs. 36.5±1.9%; P>0.05), but both are superior to Nal-IRI alone or PIC-PIT alone (viability: 75.8±2.8% vs. 53.5±4.3%, respectively; P<0.001). These observations indicate that, while combination of PIT and Nal-IRI is more effective in reducing cancer cell viability compared to their monotherapies, the co-packaging of PIC and irinotecan in a single nanoformulation may not always be required, e.g., such as in low EGFR-expressing tumors.

Combination treatments are most effective when targeting not only non-overlapping signaling pathways but also different subcellular components (Barua S, Mitragotri S, Synergistic targeting of cell membrane, cytoplasm, and nucleus of cancer cells using rod-shaped nanoparticles. ACS Nano 2013, 7:9558-9570; Fernald K, Kurokawa M, Evading apoptosis in cancer. Trends in cell biology 2013, 23:620-633). Here, three mechanistically distinct, clinically used agents (Cet, BPD, and irinotecan) were integrated into a single nanoplatform to target EGFR, mitochondria, and DNA, cooperatively. Similar to previous observations using PIC or Cet alone (Abu-Yousif A O et al., Epidermal growth factor receptor-targeted photosensitizer selectively inhibits EGFR signaling and induces targeted phototoxicity in ovarian cancer cells. Cancer letters 2012, 321:120-127; Inglut C T et al., Systematic Evaluation of Light-Activatable Biohybrids for Anti-Glioma Photodynamic Therapy. J Clin Med 2019, 8(9):1269) it was shown that PIC-Nal-IRI downregulates EGFR expression as soon as 24 hours of administration. This confirms that click conjugation of PIC onto Nal-IRI does not impair PIC's ability to inhibit EGFR.

It is well established that irinotecan-induced up-regulation of γ-H2AX, a prominent DNA damage marker, typically occurs at 48-72 hours after incubation. Here, it was shown that PIC-Nal-IRI elicits DNA breakage at 50 and 72 hours after treatment. However, it was observed that PIC-Nal-IRI transiently downregulates γ-H2AX expression in the first 24 hours of incubation. This is believed to be due to the activation of Cet-induced DNA repair pathways (e.g., Eme1) (Huang H C et al., Mechanism-informed Repurposing of Minocycline Overcomes Resistance to Topoisomerase Inhibition for Peritoneal Carcinomatosis. Mol Cancer Ther 2018, 17:508-520). Further, depolarization of mitochondria membrane was observed at 24 hours after light activation of PIC-Nal-IRI, PIC-Nal or PIC, but not with Nal-IRI alone. This indicates that cytosolic mitochondrial photodamage was achieved primarily by PIC (Inglut C T et al., Systematic Evaluation of Light-Activatable Biohybrids for Anti-Glioma Photodynamic Therapy. J Clin Med 2019, 8(9):1269).

The selectivity-uptake trade-off of photo-immunoconjugates and the need of chemotherapy to enhance treatment outcomes have previously been major hurdles limiting the application of PIT for cancer management using conventional techniques. In accordance with the present disclosure, a light-activatable nanoplatform is provided that overcome these challenges via a two-pronged approach. First, successful conjugation of PICs onto the surface of nanoliposomes overcomes the selectivity-uptake trade-off of PIC. Second, PIC-Nal-IRI offers a unique opportunity to target multiple major components of a cancer cell for synergistic therapeutic outcomes. In vitro results provide valuable parameters (e.g., size, PIC density, and PIC binding affinity) for in vivo utilization of PIC-Nal-IRI.

All identified publications and references mentioned in this specification are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. A photo-immunoconjugate formulation, comprising:
a nanoparticle carrier;
a first therapeutic agent coupled to said nanoparticle carrier;
a photosensitizer molecule coupled to a first therapeutic agent, wherein said photosensitizer is coupled to a surface of said nanoparticle carrier; and
a second therapeutic agent;
wherein said nanoparticle carrier is a polymeric nanoparticle;
wherein said first therapeutic agent is an anti-EGFR monoclonal antibody, or an antigen-binding fragment thereof;
wherein said second therapeutic agent is a topoisomerase inhibitor;
wherein the first and/or second therapeutic agent is encapsulated within said polymeric nanoparticle; and
wherein said anti-EGFR monoclonal antibody is cetuximab or panitumumab.

2. The photo-immunoconjugate formulation of claim 1, wherein said first therapeutic agent is cetuximab or antigen-binding fragment thereof.

3. The photo-immunoconjugate formulation of claim 1, wherein said anti-EGFR monoclonal antibody is panitumumab or antigen-binding fragment thereof.

4. The photo-immunoconjugate formulation of claim 1, wherein said photosensitizer molecule is a benzoporphyrin derivative (BPD) photosensitizer, a chlorin-based photosensitizer, a porphyrin-based photosensitizer, a bacteriochlorin-based photosensitizer, a phthalocyanine-based photosensitizer, or a fluorescence imaging agent.

5. The photo-immunoconjugate formulation of claim 1, wherein said topoisomerase inhibitor is selected from the group consisting of irinotecan (IRI), topotecan, and camptothecin.

6. The photo-immunoconjugate formulation of claim 1, wherein said polymeric nanoparticle is poly(lactic-co-glycolic acid) (PLGA).

7. A method of treating EGFR-receptor expressing cancer comprising administering a therapeutically effective amount of a photo-immunoconjugate formulation to a patient in need thereof, wherein said photo-immunoconjugate formulation comprises the formulation of claim 1.

8. The method of claim 7, wherein said anti-EGFR monoclonal antibody is cetuximab.

9. The method of claim 7, wherein said anti-EGFR monoclonal antibody is panitumumab.

10. The method of claim 7, wherein said formulation is administered parenteral, via injection, topically, orally, or intranasally.

11. The method of claim 7, wherein said photosensitizer molecule is a benzoporphyrin derivative (BPD) photosensitizer, a chlorin-based photosensitizer, a porphyrin-based photosensitizer, a bacteriochlorin-based photosensitizer, a phthalocyanine-based photosensitizer, or a fluorescence imaging agent.

12. The method of claim 7, wherein said topoisomerase inhibitor is selected from the group consisting of irinotecan (IRI), topotecan, and camptothecin.

13. The method of claim 7, wherein said cancer is selected from the group consisting of head and neck cancer, ovarian cancer, glioblastoma, gastrointestinal cancer, pancreatic cancer, breast cancer, lung cancer, prostate cancer, bladder cancer, and colorectal cancer.

14. The method of claim 7, further comprising photoactivating said photosensitizer molecule.

\* \* \* \* \*